(12) United States Patent
Kramer et al.

(10) Patent No.: US 9,925,291 B2
(45) Date of Patent: Mar. 27, 2018

(54) AIR FRESHENER CANISTERS

(71) Applicant: WK Holdings, Inc., Monroe, NY (US)

(72) Inventors: Heidi Kramer, Monroe, NY (US);
Elimelech Wagschal, Monroe, NY (US)

(73) Assignee: WK Holdings, Inc., Monroe, NY (US)

( * ) Notice: Subject to any disclaimer, the term of this patent is extended or adjusted under 35 U.S.C. 154(b) by 23 days.

(21) Appl. No.: 15/186,778

(22) Filed: Jun. 20, 2016

(65) Prior Publication Data

US 2016/0287739 A1    Oct. 6, 2016

Related U.S. Application Data

(63) Continuation of application No. 14/304,884, filed on Jun. 14, 2014, now Pat. No. 9,370,598, which is a continuation-in-part of application No. 29/458,128, filed on Jun. 17, 2013, now Pat. No. Des. 761,408.

(60) Provisional application No. 61/835,834, filed on Jun. 17, 2013.

(51) Int. Cl.
*A24F 25/00* (2006.01)
*A61L 9/12* (2006.01)

(52) U.S. Cl.
CPC ............... *A61L 9/127* (2013.01); *A61L 9/12* (2013.01)

(58) Field of Classification Search
CPC . B60H 2003/0064; B60H 3/0007; A61F 9/04; A61F 9/127; A61F 9/12; A61F 9/125; A01M 1/2044
USPC ........................................................ 239/44
See application file for complete search history.

(56) References Cited

U.S. PATENT DOCUMENTS

| 2,500,896 A | 3/1950 | Drake |
| 4,155,500 A | 5/1979 | Dutcher |
| 4,323,193 A * | 4/1982 | Compton ............... A61L 9/127 239/44 |

(Continued)

FOREIGN PATENT DOCUMENTS

| EP | 1661588 A1 | 5/2006 |
| WO | 8500290 A1 | 1/1985 |

(Continued)

OTHER PUBLICATIONS http://www.amazon.com/Amini-Chrystal-Designer-Freshener-Fragrance/dp/B008F8G5DU/ref=sr_1_80?ie=UTF8&qid=1370691098&sr=8-80&keyword s=hanging+car+air+freshener.

(Continued)

*Primary Examiner* — Davis Hwu
(74) *Attorney, Agent, or Firm* — Merchant & Gould P.C.

(57) ABSTRACT

An air freshener canister includes a container, a nipple thereon and a cap threadably matable therewith. The cap can be positioned along the length of the nipple from a closed position with the cap rim against the exterior surface of the container and an open position wherein there is spacing between the rim and exterior surface. A volatile liquid in the container emits air freshener vapors. A wick runs from the liquid to the nipple. When the cap is in the open position, vapors escape from the wick through the spacing. When the cap is in the closed position the vapors are prevented from escaping. When the cap is removed from the nipple the container may be refilled with the volatile liquid. The escape of vapors may be increased or decreased by positioning the cap on the nipple to increase or decrease the spacing.

13 Claims, 21 Drawing Sheets

(56) References Cited

U.S. PATENT DOCUMENTS

| | | |
|---|---|---|
| 4,739,928 A | 4/1988 | O'Neil |
| D321,320 S | 11/1991 | Halm |
| 5,219,121 A * | 6/1993 | Fox .................. A01M 1/2044 239/34 |
| D364,451 S | 11/1995 | Rosenschein |
| D393,063 S | 3/1998 | Wefler |
| 5,832,648 A | 11/1998 | Malone |
| 5,906,298 A | 5/1999 | Ward |
| 6,085,989 A | 7/2000 | Cox |
| 6,158,668 A | 12/2000 | Burgeson |
| 6,202,938 B1 | 3/2001 | Collier |
| 6,241,161 B1 | 6/2001 | Corbett |
| 6,352,210 B1 | 3/2002 | Requejo |
| 6,513,726 B1 | 2/2003 | Esteban Duran |
| 6,514,467 B1 | 2/2003 | Bulsink et al. |
| 6,565,012 B1 | 5/2003 | Zaragoza et al. |
| 6,648,239 B1 | 11/2003 | Myny et al. |
| 6,722,577 B2 | 4/2004 | Dobyns, III |
| 6,755,351 B2 | 6/2004 | Giovannone |
| D509,891 S | 9/2005 | Rymer |
| 6,938,833 B2 | 9/2005 | Chen |
| 7,025,283 B2 | 4/2006 | Torres |
| 7,140,553 B2 | 11/2006 | Zobele |
| 7,185,827 B2 | 3/2007 | Quintard et al. |
| 7,243,859 B2 | 7/2007 | Caserta et al. |
| D565,715 S | 4/2008 | Wu |
| D583,037 S | 12/2008 | Kenny |
| D588,688 S | 3/2009 | Lablaine |
| 7,780,094 B2 * | 8/2010 | Caserta ............. A61L 9/127 239/289 |
| 7,837,930 B2 | 11/2010 | Grodsky |
| D666,284 S | 8/2012 | Robinson et al. |
| 8,251,299 B1 | 8/2012 | Irvin |
| D686,719 S | 7/2013 | Lin |
| D708,728 S | 7/2014 | Yoo et al. |
| 8,893,985 B2 * | 11/2014 | Wu ..................... A61L 9/04 222/182 |
| 2002/0109013 A1 | 8/2002 | Desrosiers |
| 2003/0080197 A1 | 5/2003 | Tuomikoski et al. |
| 2003/0098362 A1 | 5/2003 | Chuang |
| 2007/0252016 A1 | 11/2007 | Chen |
| 2008/0169220 A1 | 7/2008 | Gaines |
| 2009/0218413 A1 | 9/2009 | Withers |
| 2009/0261179 A1 | 10/2009 | Hall |
| 2010/0326280 A1 | 12/2010 | Hicks |
| 2011/0036922 A1 | 2/2011 | Bulsink |
| 2011/0139884 A1 | 6/2011 | Gasper et al. |
| 2011/0303760 A1 | 12/2011 | Joshi et al. |
| 2014/0175189 A1 | 6/2014 | Stephenson |
| 2015/0060564 A1 | 3/2015 | Bowles |
| 2015/0096218 A1 | 4/2015 | Burr |
| 2015/0137395 A1 | 5/2015 | Wolf et al. |
| 2015/0202340 A1 | 7/2015 | Warberg Block |
| 2015/0314031 A1 | 11/2015 | Torres |

FOREIGN PATENT DOCUMENTS

| | | |
|---|---|---|
| WO | 14176291 A1 | 10/2014 |
| WO | 16003459 A1 | 1/2016 |

OTHER PUBLICATIONS http://www.ebay.com/itm/Exfresh-Air-Freshener-Liquid-Jewel-Apple-Cinnamon-/300746839700.
http://www.alibaba.com/product-gs/509085262/Hanging_Liquid_Car_Air_Freshener.html.
http://www.alibaba.com/product-gs/580513369/2013_Newest_Design_8ml_Cute_Hanging.html.
http://www.alibaba.com/product-gs/948693446/2013_fashion_car_hanging_perfume_air.html.
http://www.alibaba.com/product-gs/555737413/2013_colorful_luxury_car_air_freshener.html.

* cited by examiner

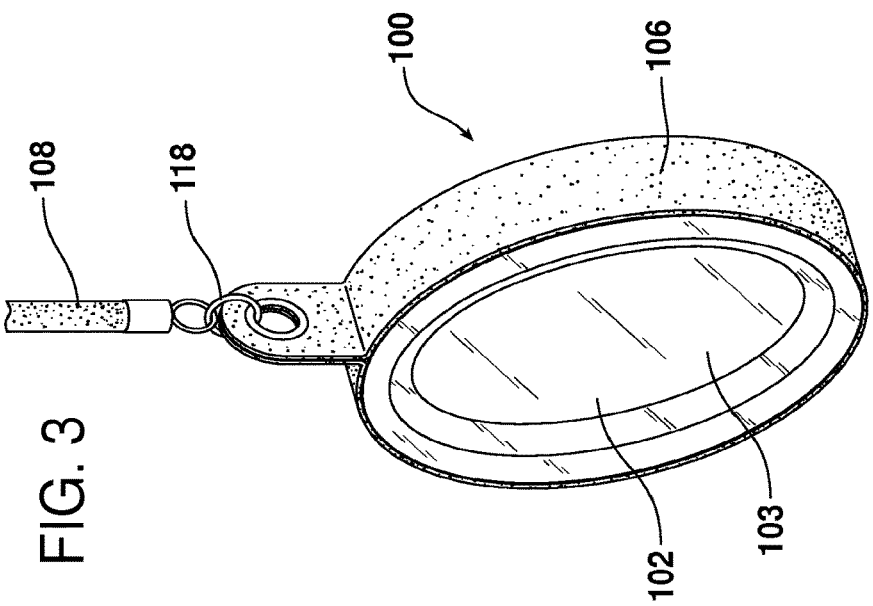
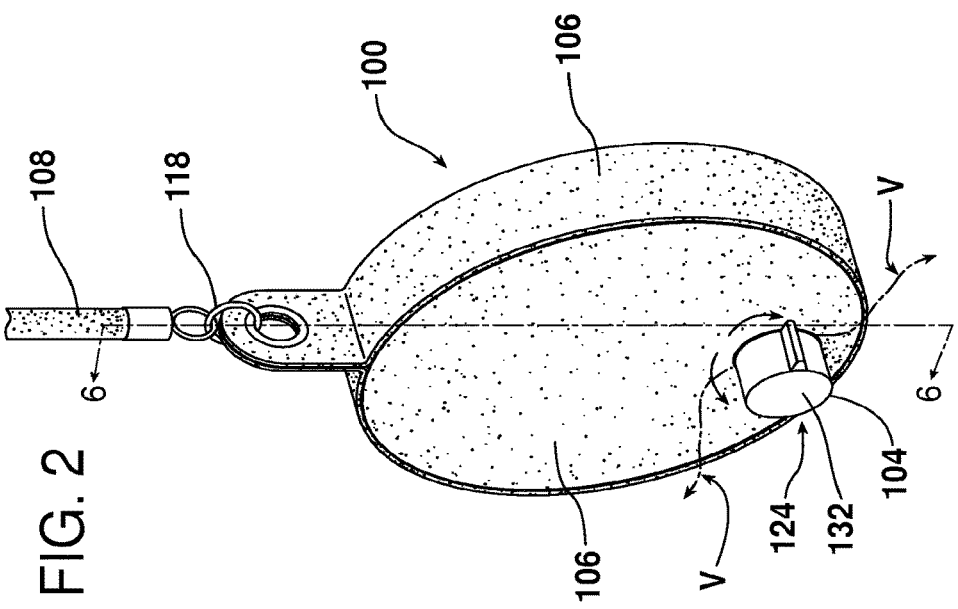

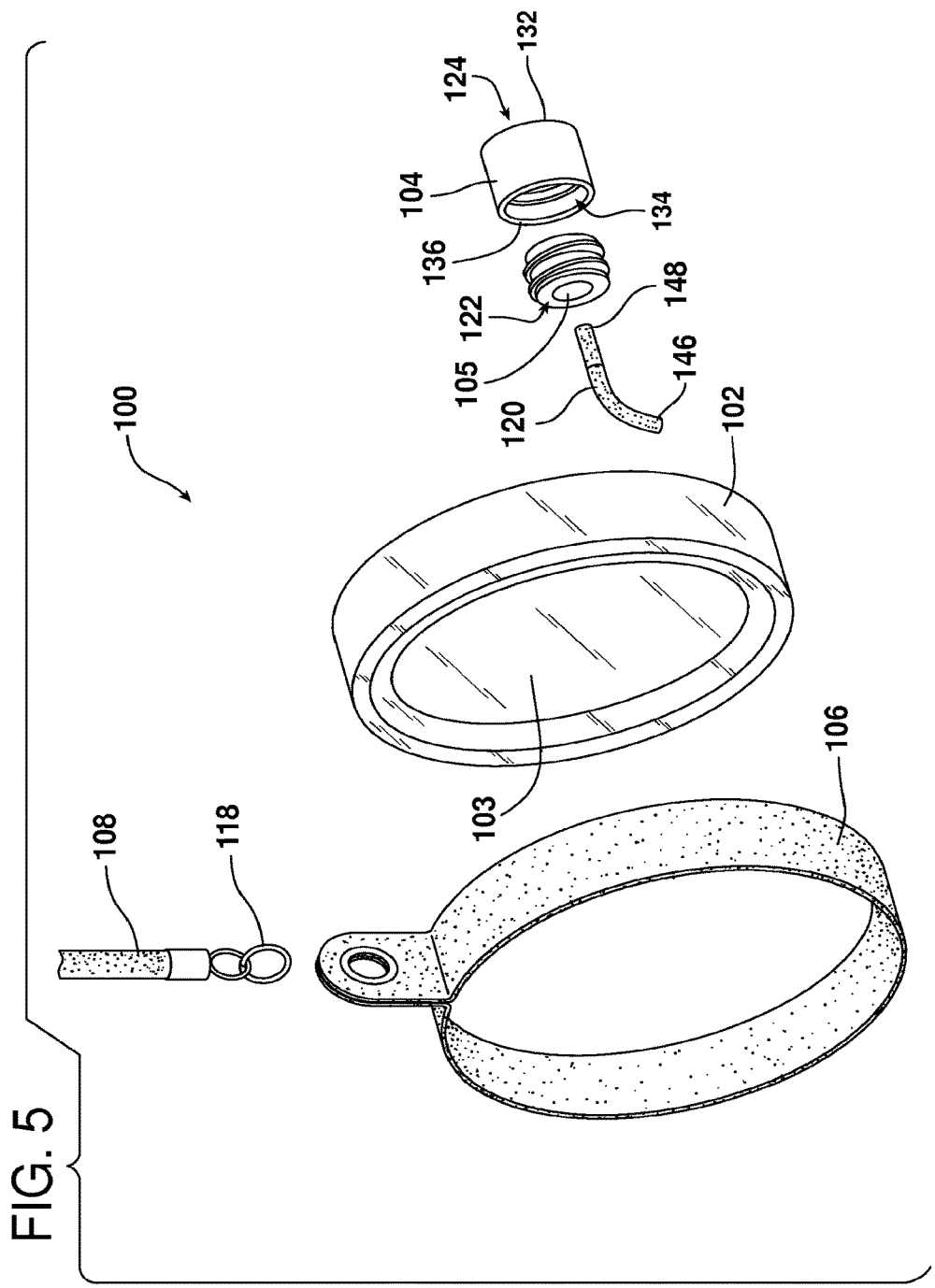

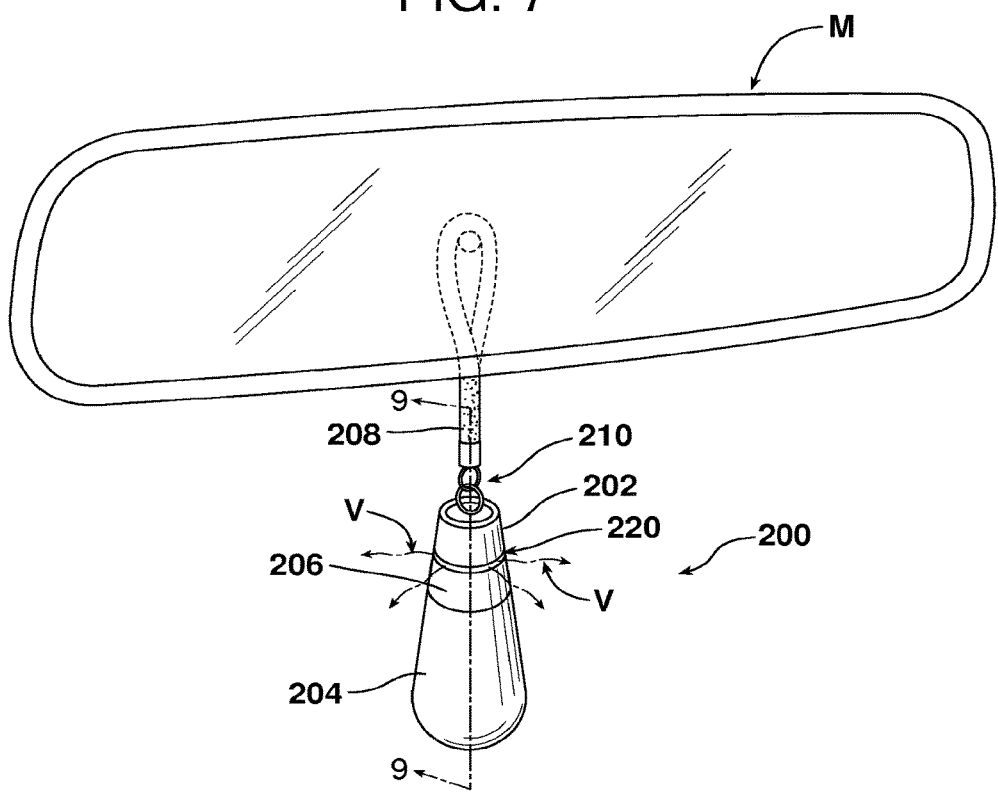

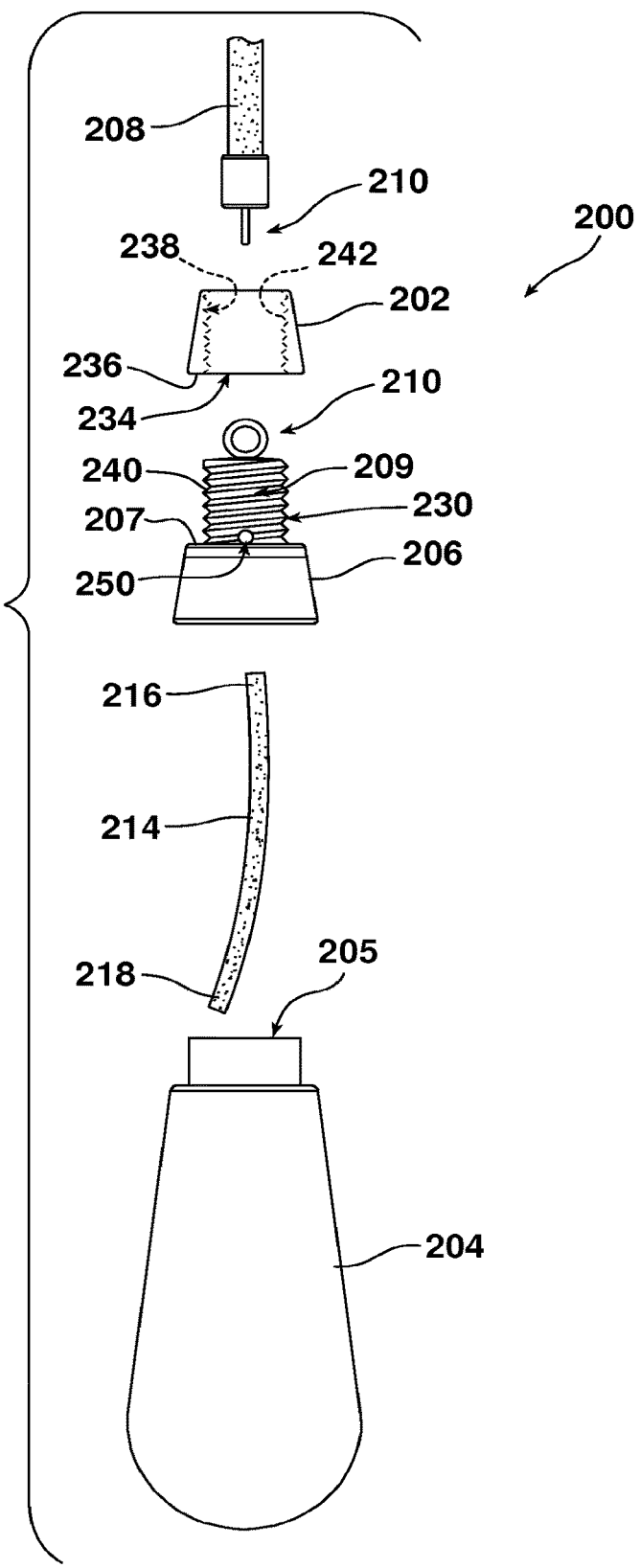

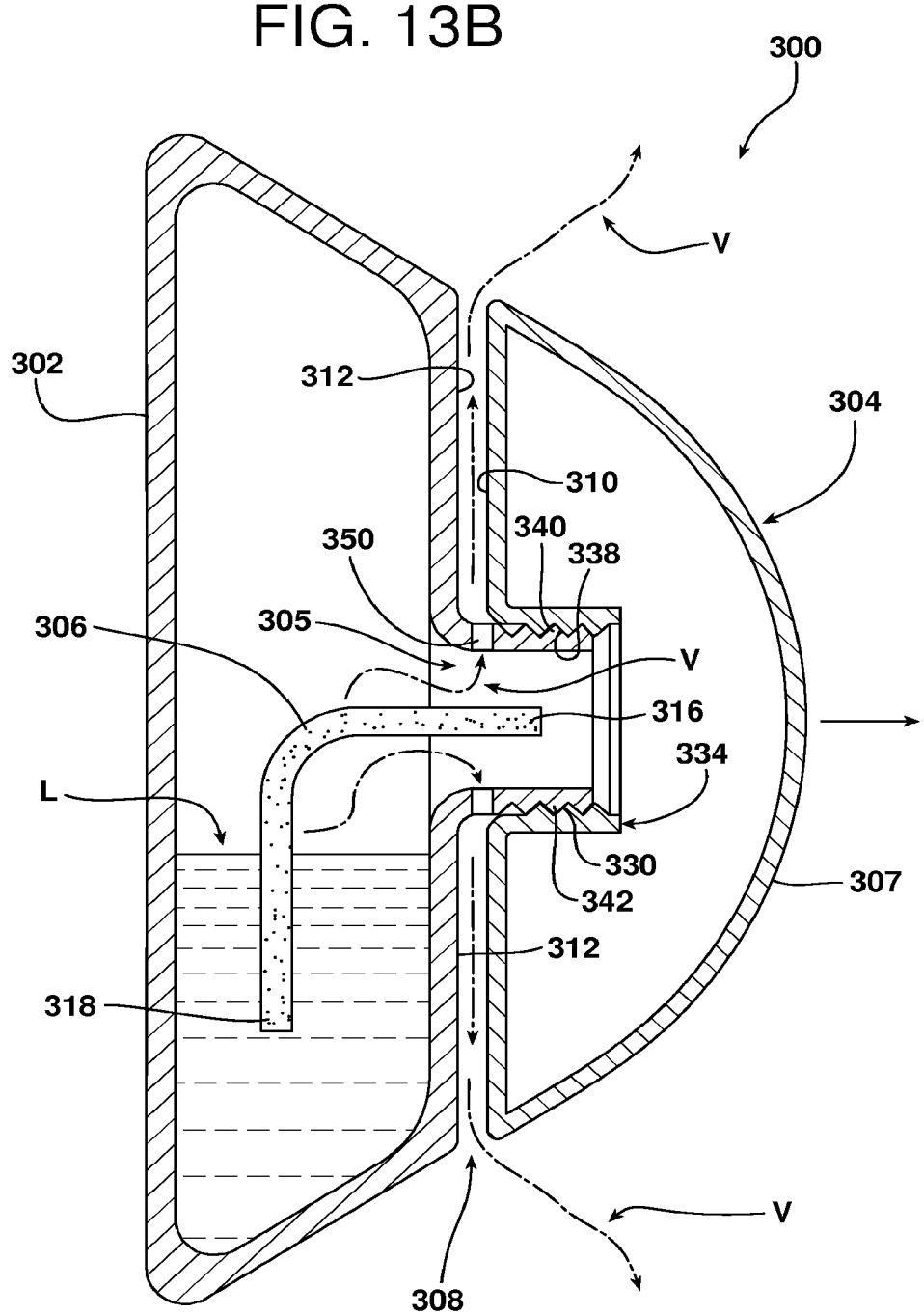

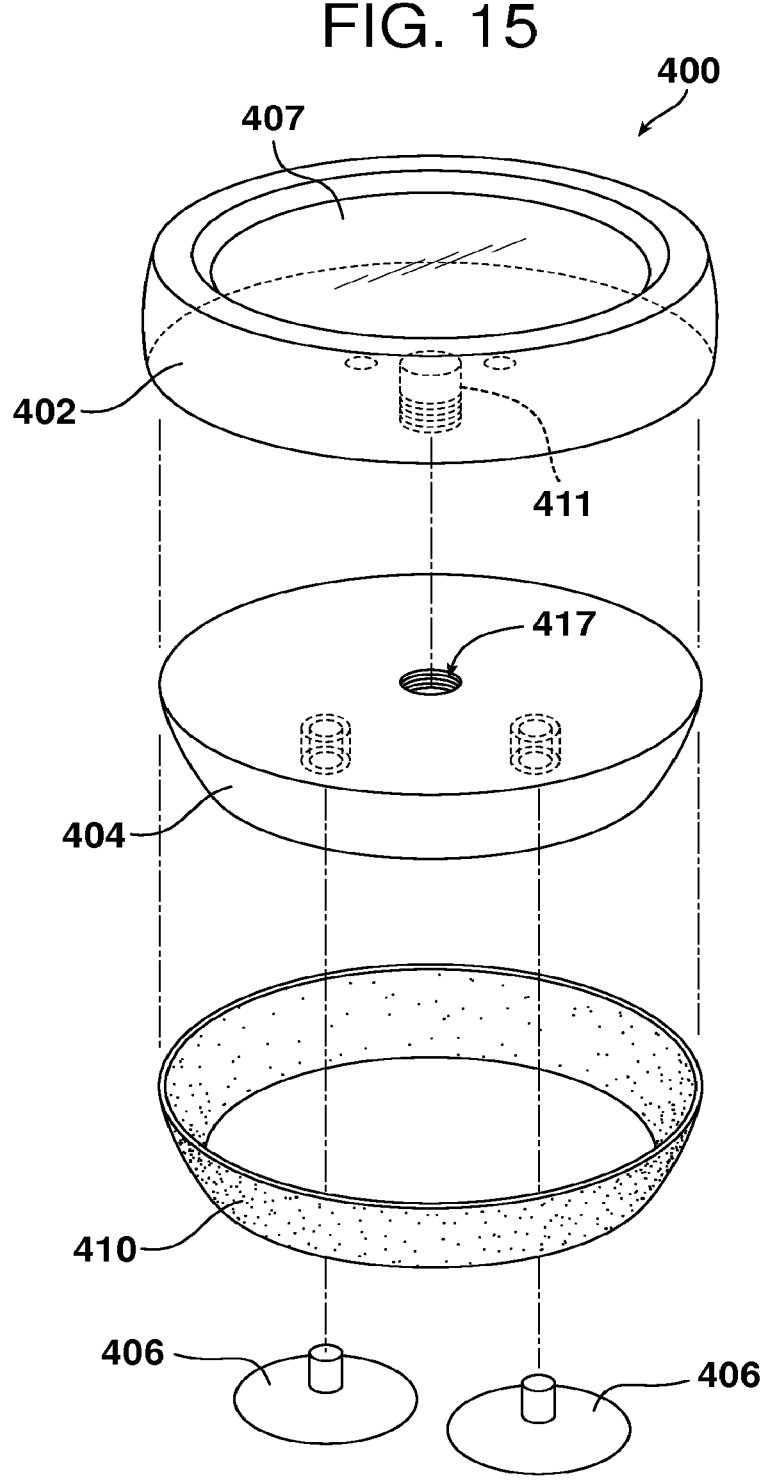

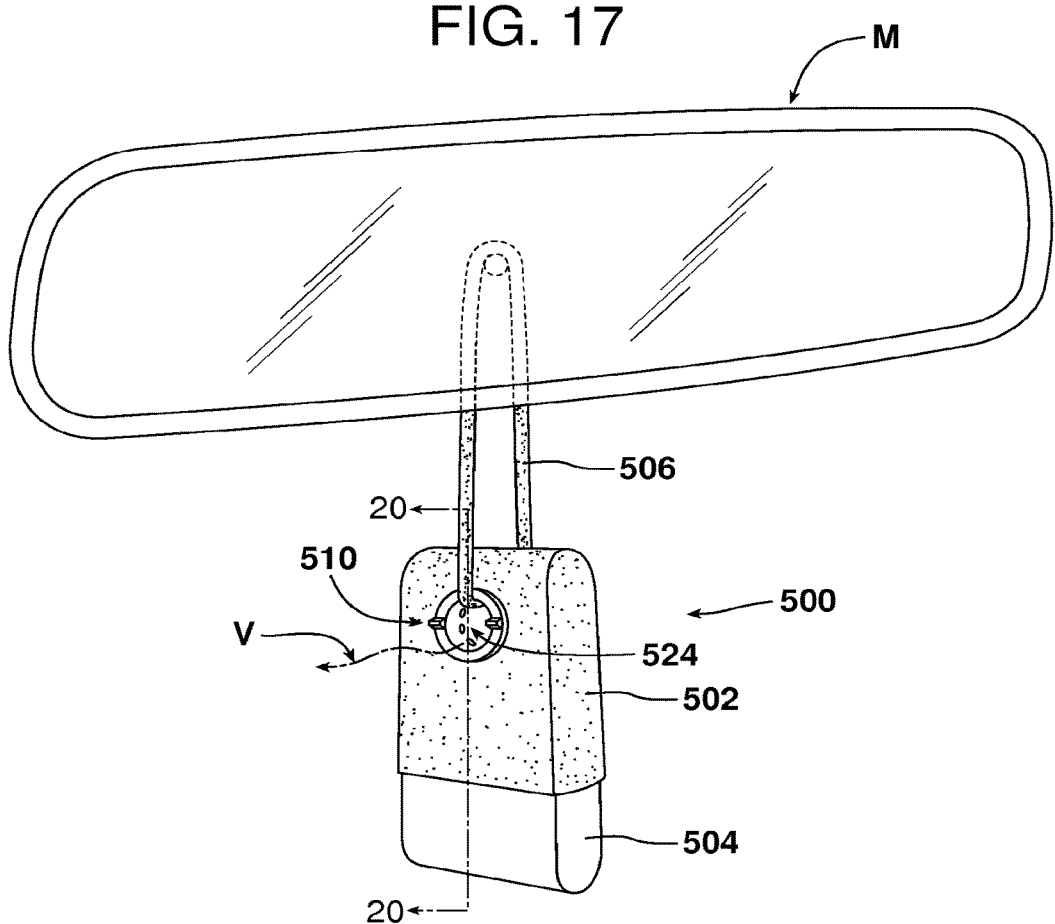
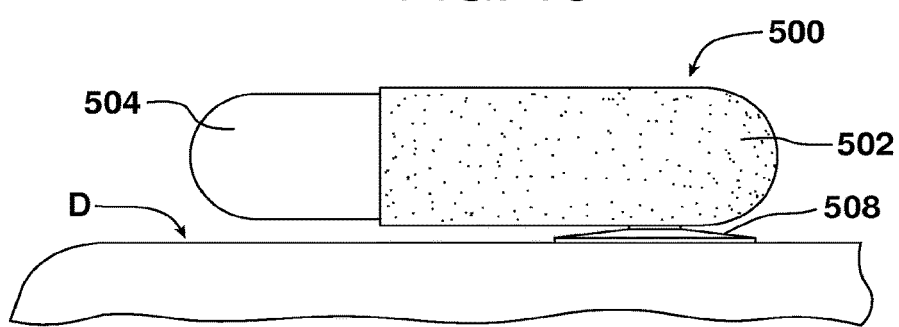

AIR FRESHENER CANISTERS

RELATED APPLICATIONS

This application is a continuation of application Ser. No. 14/304,884 filed Jun. 14, 2014 (pending), which is a Non-Provisional Patent Application claiming priority of Provisional Patent Application 61/835,834 filed on Jun. 17, 2013 and a Continuation-in-Part application of U.S. Ser. No. 29/458,128 filed on Jun. 17, 2013, the entire disclosure of each of these applications is incorporated herein by reference.

FIELD OF THE INVENTION

This invention relates to air freshener canisters, and in particular decorative, refillable canisters having a controlled release of air freshener vapors into the environment that are suitable for use in enclosed spaces, such as motor vehicles, bathrooms and other rooms of residential or commercial establishments.

BACKGROUND OF THE INVENTION

Various different types of air fresheners or air freshener devices exist for dispensing a variety of different compositions into the environment. Most of these devices rely on evaporation from a solid or liquid air freshener composition to produce a vapor that goes into the air.

Some of the currently available evaporation type air fresheners have a compartment that contains an air freshener composition that when exposed to the atmosphere the composition evaporates. Typically, the composition from the compartment is at a rate that is dependent on the rate of movement of the air over the compartment. Such devices are not adjustable, in that the rate at which the composition evaporates is dependent solely on the environmental conditions, e.g., primarily air flow and to some degree temperature.

In some devices, an air freshener composition that vaporizes is incorporated into a solid carrier from which the substance evaporates and enters the atmosphere, frequently, after a protective wrapping or cover is opened or removed. Typical of such devices is the ubiquitous, unattractive hanging card air freshener that hangs, for example, from the rear-view mirror or air conditioning vent of an automobile. The effectiveness of these devices is not adjustable, highly dependent on the environmental conditions in the automobile and gradually diminishes in effectiveness over time.

Pumps and aerosol sprays exist that emit air freshener or air freshener compositions. However, these may be dangerous to keep in a hot automobile interior, as the pressurized container may become over pressurized, and possibly leak or explode, or otherwise become damaged. In addition, these liquids or gasses can damage the interior surfaces of an automobile and may be explosive under certain conditions.

In spite of these numerous devices, there is still a need for an air freshener device that enables the selective, controlled release of vapors into the atmosphere, is refillable, is attractive and can be positioned at various locations in, for example, an automobile.

There is also a need for an air freshener device that is attractive for use in, for example, offices, automobiles, etc. that can be branded with, for example luxury brand logos and designs, whether original or under license from the brand owner.

Applicant is aware of the following US design patents:

U.S. D321320 to Halm shows a liquid detergent dispenser, apparently used to contain a detergent from which it can be poured.

U.S. D364451 to Rosenschein shows a conically shaped air freshener with an eyelet on the apex.

U.S. D393063 to Weller shows rectangular shaped volatile liquid dispenser with openings on the top thereof.

U.S. D666284 to Robinson shows a disc shaped air freshener with openings on both sides of the disc and clips on one side, apparently used to attach the air freshener to an object.

None of these design patents teach any functionality for selectively permitting or preventing the release of vapors from the device.

Applicant is aware of the following US patents:

U.S. Pat. No. 6,938,833 to Chen discloses a vehicle air freshener that includes a bottle holding a color fluid and a volatile liquid perfume floating thereon. A socket is fastened to the bottle neck that holds an absorptive member that dissipates the volatile liquid perfume into air. There is a weight on the bottom of the bottle. The air freshener is designed to oscillate like a toy tumbler and dissipate the volatile liquid perfume into the air inside the vehicle during running of the vehicle.

U.S. Pat. No. 6,755,351 to Giovannone discloses a container having a liquid perfume therein. The container has a stopper one or more threadlike elements, functioning as a hanging means, which pass through the stopper. A section of the thread comes into contact with the perfume which is absorbed therein. The perfume propagates through the thread to emit the air freshener into the air.

U.S. Pat. No. 6,722,577 to Dobyns discloses an aromatic liquid dispensed in a vapor phase from a container holding the liquid. The container is in a conical form and has a controlled opening through which the liquid is dripped downwardly onto a substrate, from which it is dispensed in vapor phase into the atmosphere. The dispenser is configured such that it may stand on a flat surface or may be hung, e.g., a closet, automobile, or the like.

U.S. Pat. No. 4,155,500 to Dutcher discloses a carton constructed from a one-piece, paperboard blank for receiving an air freshener cake. The carton has a front panel with openings through which the cake material is diffused.

U.S. Pat. No. 2,500,896 to Drake discloses a hanging aromatic dispenser for mounting in a ventilating air stream to evaporate a controlled amount of a liquid aromatic from the device. Liquid aromatics are placed in a reservoir case which is suspended in the air stream. A knob is then turned to bring a lower moistened part of a disk shaped wick to the top of the reservoir case into the evaporative area. This also opens a number of holes in the top of the reservoir case. Air enters the evaporative area, takes up a portion of the liquid on the wick and then exits thru the holes.

US 2011/0036922 to Bulsink discloses an air-freshener for a vehicle provided with a housing into which a container for a liquid containing a volatile component can be inserted. A wick extends into the housing. The housing includes a sideways movable covering cap which can cover the wick entirely or partially.

US 2010/0326280 to Hicks disclose an electrically powered air freshener for motor vehicles. The air freshener has containers that contain an air freshener substance that can evaporate from the container, and can be displaced from the air freshener via a fan. The motor and fan of the air freshener may be turned on, off, or the speed of the fan can be controlled.

US 2009/0218413 to Withers discloses dispenser for dispensing at least two compositions stored in a dispenser, each in a separate compartment. The dispenser has an adjustable discharging mechanism for each composition.

US 2007/0252016 to Chen disclose a perfume device having a changeable appearance that may be worn. The device includes a casing having a fan therein and on/off switch and a replaceable/changeable decoration plate. The casing includes a plurality of air outlets with perfume therein. A clip permits attachment to apparel.

US 2003/0012680 to Balsys discloses an odorizer/deodorizer device that includes two shells forming a housing. A scented insert is disposed within the housing. The insert may be an absorbent pad containing a liquid-based scent. An end of the housing is configured to be securely positioned in alignment with a fan outlet of an electrical device. The housing includes vents to allow air to be forced therethrough. The scented insert may also include apertures to facilitate the flow of air therethrough so that as the fan is in operation, the air forced therethrough is odorized or deodorized.

WO 8500290 A to Dessimond discloses a hanging diffuser for liquid scent that has a diffusion rate control located on the front of the device.

EP 1661588 to Cipolla discloses a container for diffusion of volatile liquids that hangs from a cord.

Applicant is aware of the following non-patent references:
1. http://www.amazon.com/Amini-Chrystal-Designer-Freshener-Air freshener/dp/B008F8G5DU/ref=sr_1_80?ie=UTF8&qid=1370691098&sr=8-80&keywords=hanging+car+air+freshener
2. http://www.ebay.com/itm/EXFRESH-Air-Freshener-Liquid-Jewel-APPLE-CINNAMON-/300746839700
3. http://www.alibaba.com/product-gs/509085262/Hanging_Liquid_Car_Air_Freshener.html
4. http://www.alibaba.com/product-gs/580513369/2013_Newest_Design_8ml_Cute_Hanging.html
5. http://www.alibaba.com/product-gs/948693446/2013_fashion_car_hanging_perfume_air.html
6. http://www.alibaba.com/product-gs/555737413/2013_colorful_luxury_car_air_freshener.html None of the references teach or suggest the air freshener canisters of this invention.

OBJECTS AND SUMMARY OF THE INVENTION

It is an object of this invention to provide a canister shaped air freshener, wherein the air freshener vapors are released by the turning of a section of the canister to expose the vent openings to the interior of the canister to enable the air freshener to be emitted therefrom.

It is another object of the present invention to provide a simplified and improved canister and dispenser for the dispensing of volatile aromatic vapor into the air.

It is an additional object of the present invention to provide an air freshener canister that contains a liquid volatile composition that is spill-proof, an important factor when used in automobiles.

It is an additional object of the present invention to provide an improved air freshener canister that enables the air freshener vapors and level to be dispensed in an adjustable, controlled and uniform manner.

It is a further object to provide an air freshener device that enables the selective, controlled release of vapors into the atmosphere, is refillable, is attractive and can be positioned at various locations in, for example, an automobile.

It is also an object of this invention to provide an air freshener that can be made in various sizes and shapes.

It is also an object of this invention to provide an air freshener device that is attractive for use in, for example, offices, automobiles, etc. that can be branded with, for example luxury brand logos and designs, whether original or under license from the brand owner.

In one embodiment of this invention, an air freshener canister includes a container having an exterior surface and a mouth opening through the exterior surface. A nipple on the exterior surface of the container extends from the mouth opening, the nipple having an interior surface and an exterior surface. A cap is provided that has a closed end, an open end, a rim around the open end and an interior surface. The interior surface of the cap is slidably engagable with the exterior surface of the nipple, preferably with mating threads, to enable the cap to be selectively positioned along the length of the nipple. The cap may be positioned between a closed position wherein the rim is juxtaposed against the exterior surface of the container, an open position wherein there is a spacing between the rim and the exterior surface of the container, and a refill position wherein the cap has been removed from the nipple. There is a volatile liquid composition within the container that emits air freshener vapors and a wick for absorbing the volatile liquid. The wick has one end and a portion of the length of the wick surrounded by and in contact with the volatile liquid composition, and the second end and a remaining portion of the wick extending into the nipple.

Thus, when the cap is in the open position, air freshener vapors escape from the volatile liquid composition absorbed on the wick through the spacing between the rim and the exterior surface of the container into the air. When the cap is in the closed position the air freshener vapors are prevented from escaping. When the cap is removed from the nipple the container may be refilled with the volatile liquid composition. The spacing between the rim and exterior surface of the container may be increased or decreased by selectively positioning the cap on the nipple to thereby increase or decrease the escape of air freshener vapors through the spacing into the air.

In another embodiment, an air freshener canister includes a container having an exterior surface and a mouth opening through the exterior surface. A nipple is provided on the exterior surface of the container that extends from the mouth opening, the nipple having an interior surface and an exterior surface. There is a volatile liquid composition within the container that emits air freshener vapors and a wick for absorbing the volatile liquid. The wick has one end and a portion of the length of the wick surrounded by and in contact with the volatile liquid composition, and the second end and a remaining portion of the wick extending into the nipple. A cap is provided that is removably matable with the exterior surface of the container and encloses the nipple. The cap has a cylindrical passageway therethrough having at least one vent hole that permits the passage of air freshener vapors therethrough from the wick. A drum is provided that is rotatably engagable within the cylindrical passageway. The drum has at least one vent hole. The drum is selectively rotatable from an open position and a closed position, wherein in the open position the vent holes in the cap and drum are aligned to permit the passage of air freshener vapors therethrough into the air. When the drum is in the closed position, the holes in the drum and passageway are not aligned, preventing the passage of air vapors therethrough. When the cap is in the open position air freshener vapors escape from the volatile liquid composition absorbed on the wick through the vent holes into the air and when in the closed position air freshener vapors are prevented from escaping. When the cap is removed from the container, the container may be refilled with the volatile liquid composition. Preferably the cylindrical passageway and drum each have a plurality of vent holes therein that are arranged to permit selective alignment of the vent holes to selectively increase and decrease the escape of air freshener vapors into the air.

Other features and advantages of the present invention will become apparent from the following more detailed description, taken in connection with the accompanying drawings, which illustrate other embodiments, by way of example, and the principles of the invention.

BRIEF DESCRIPTION OF THE DRAWINGS

Further aspects, features and advantages of the present invention will become even more apparent with reference to the following detailed description and the accompanying drawings of several embodiments of the invention.

First Embodiment

FIG. 2 is another front perspective view of the air freshener canister 100 depicted in FIG. 1.

FIG. 3 is a rear perspective view of the air freshener canister 100 depicted in FIGS. 1 and 2.

FIG. 5 is an exploded perspective view showing all of the elements of the air freshener canister 100 depicted in this embodiment.

Second Embodiment

FIG. 7 is perspective view of the Tear Drop Air Freshener Canister 200, in use suspended by a cord 208 from the rear view mirror M of an automobile.

FIG. 8 is an exploded view showing all of the elements of the air freshener canister 200 depicted in this embodiment.

Figure 9A:
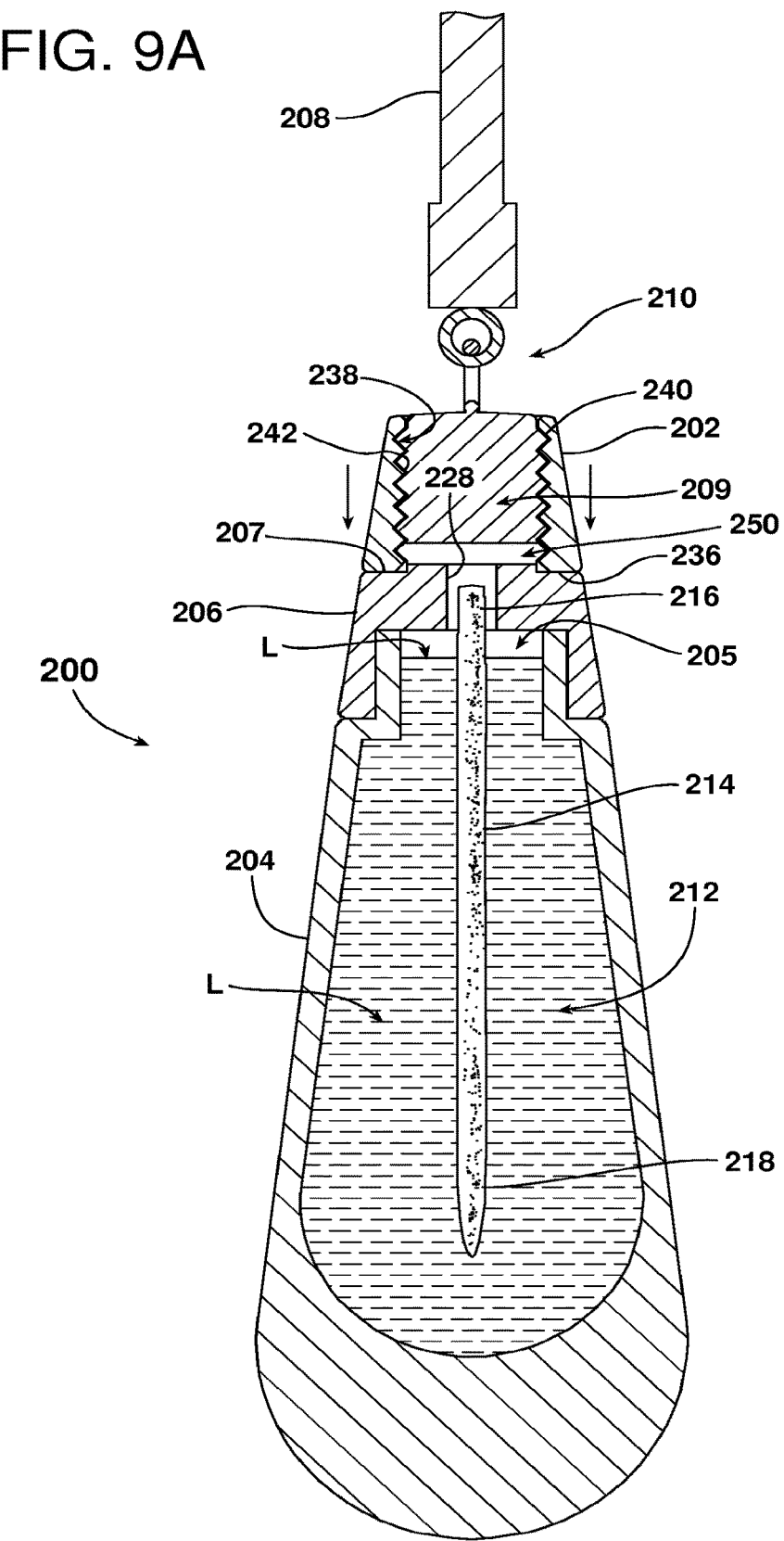

FIG. 9A is cross-sectional taken along lines 9-9 of FIG. 7 with the air freshener canister 200 in the closed position to prevent the escape of vapor V from the canister.

Figure 9B:
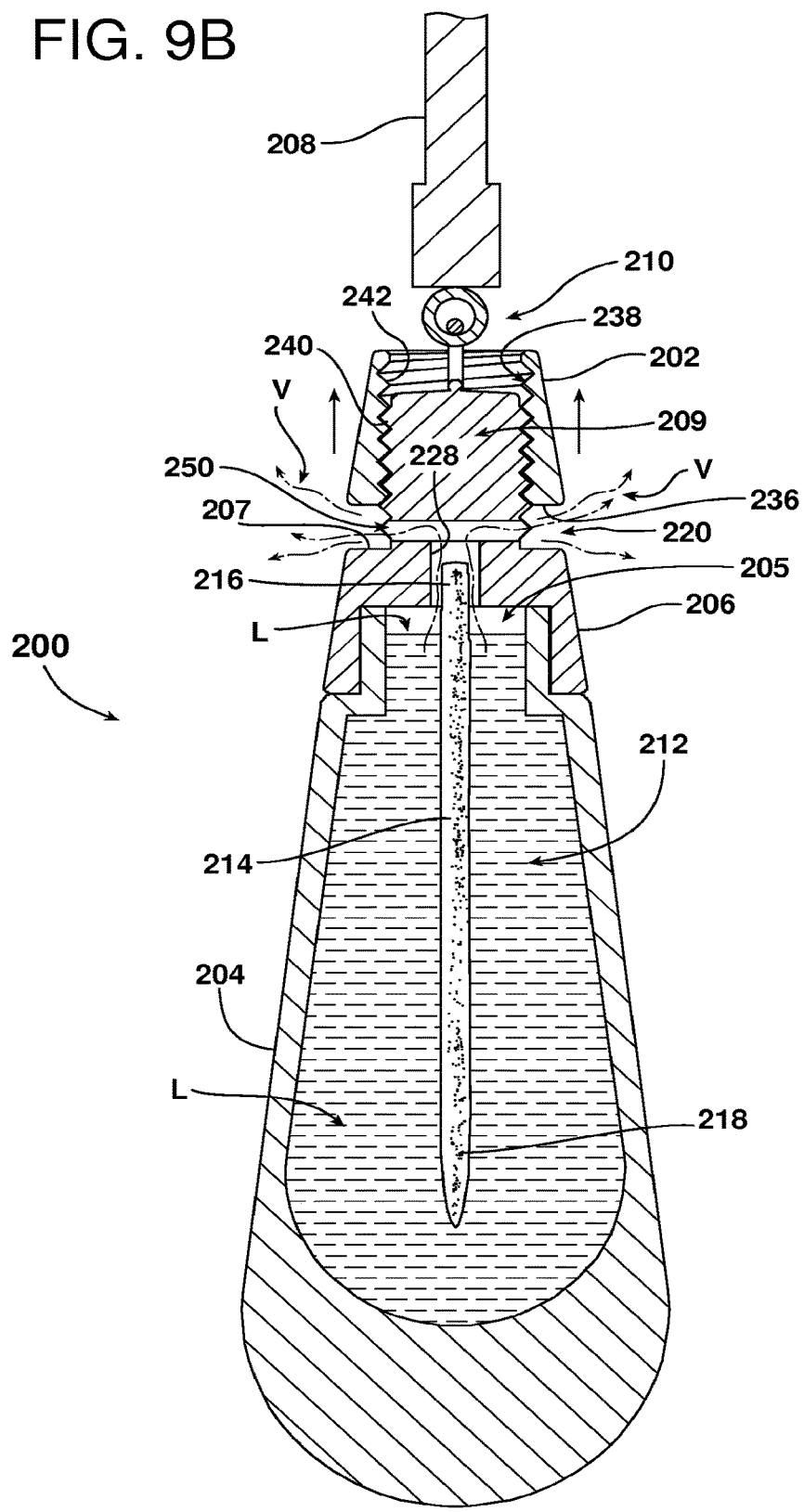

FIG. 9B is cross-sectional taken along lines 9-9 of FIG. 7 with the air freshener canister 200 in the open position to permit the escape of vapor V from the canister.

Third Embodiment

Figure 10:
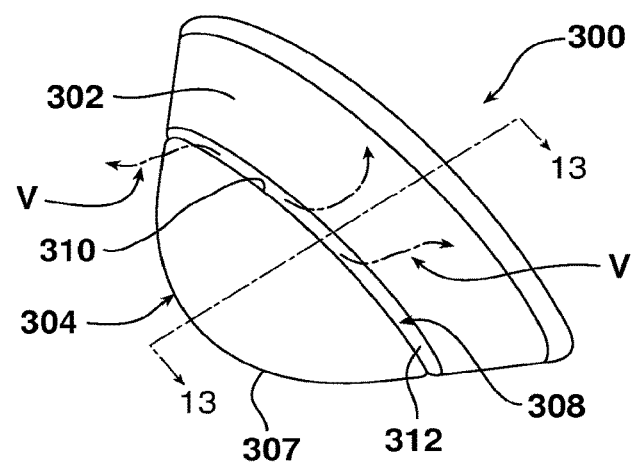

FIG. 10 is a side-view of the Front Dash Board Air Freshener Canister 300.

Figure 11:
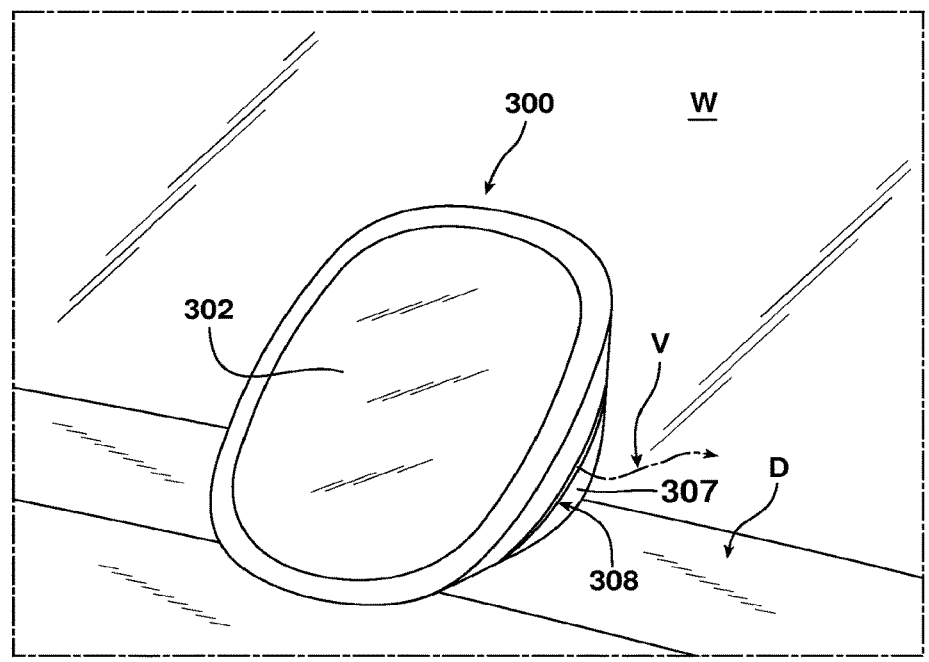

FIG. 11 is a perspective view of this embodiment of the air freshener canister 300 mounted between the dashboard D and front window W of an automobile.

Figure 12:
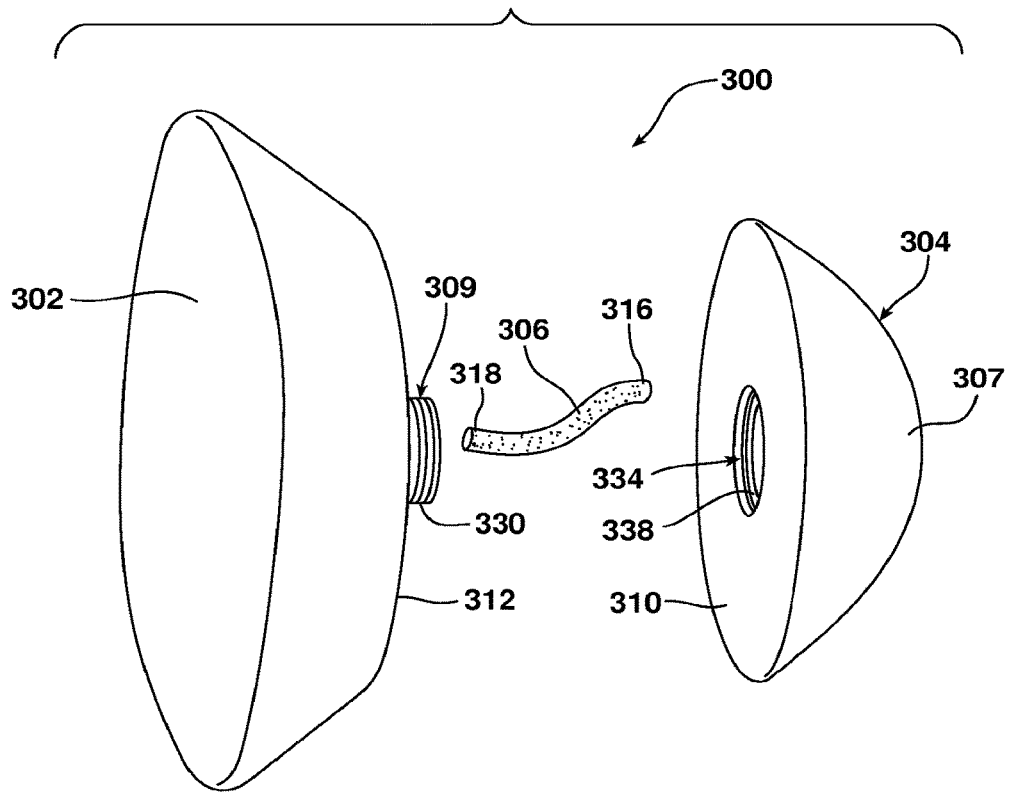

FIG. 12 is an exploded view showing all of the elements of the air freshener canister 300 depicted in this embodiment.

Figure 13A:
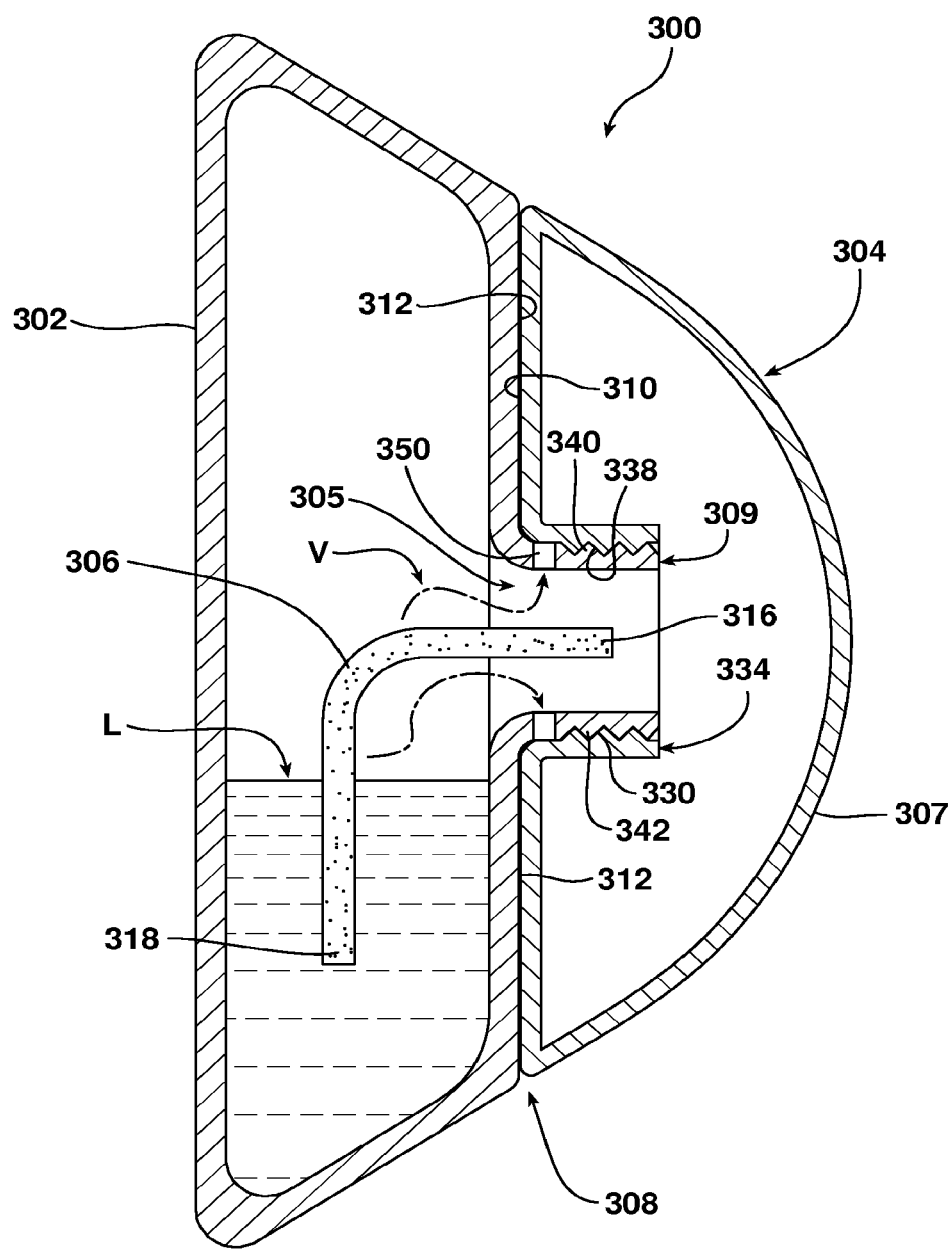

FIG. 13A is cross-sectional taken along lines 13-13 of FIG. 10 with the air freshener canister 300 in the closed position to prevent the escape of vapor V from the canister.

FIG. 13B is cross-sectional taken along lines 13-13 of FIG. 10 with the air freshener canister 300 in the open position to permit the escape of vapor V from the canister.

Fourth Embodiment

Figure 14:
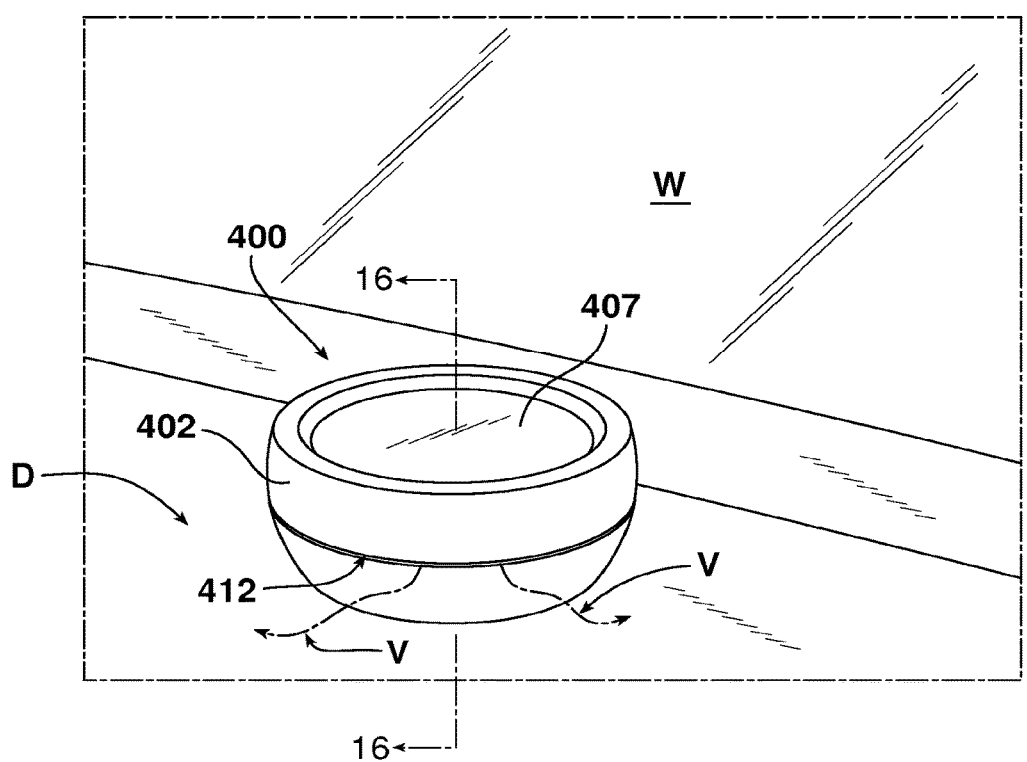

FIG. 14 is a perspective view of the Dash Board Air Freshener canister 400 mounted on the dashboard D near the front window W of an automobile.

FIG. 15 is an exploded view showing all of the elements of the air freshener canister 400 depicted in this embodiment.

Figure 16A:
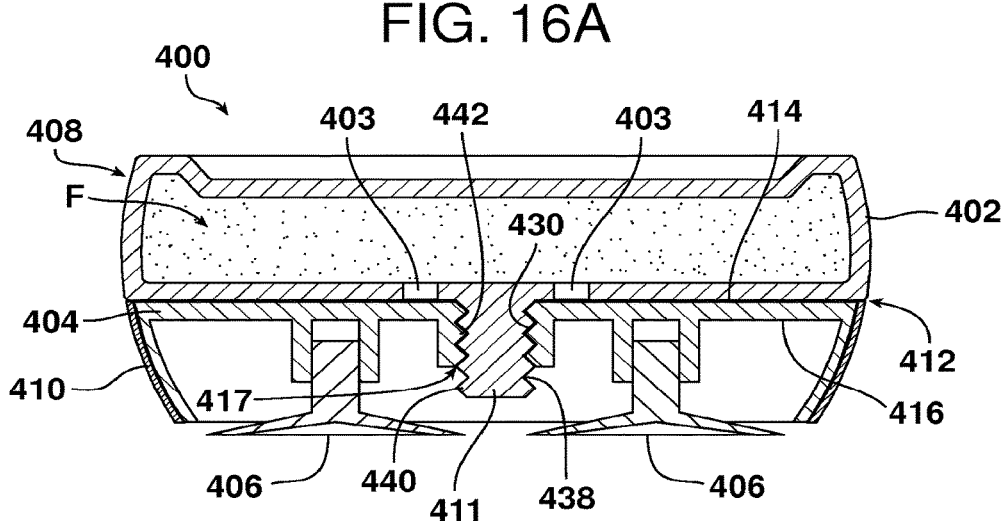

FIG. 16A is cross-sectional taken along lines 16-16 of FIG. 14 with the air freshener canister 400 in the closed position to prevent the escape of vapor V from the canister.

Figure 16B:
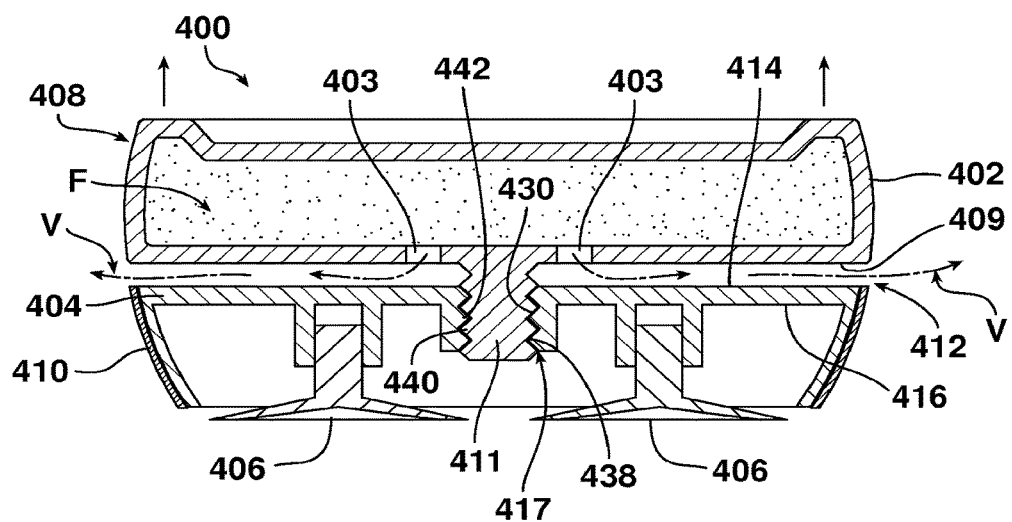

FIG. 16B is cross-sectional taken along lines 16-16 of FIG. 14 with the air freshener canister 400 in the open position to permit the escape of vapor V from the canister.

Fifth Embodiment

FIG. 17 is perspective view of the Convertible Air Freshener Canister 500, in use suspended by cord 506 from the rear view mirror M of an automobile.

FIG. 18 is side view of the air freshener canister 500 mounted on a dashboard D.

Figure 19:
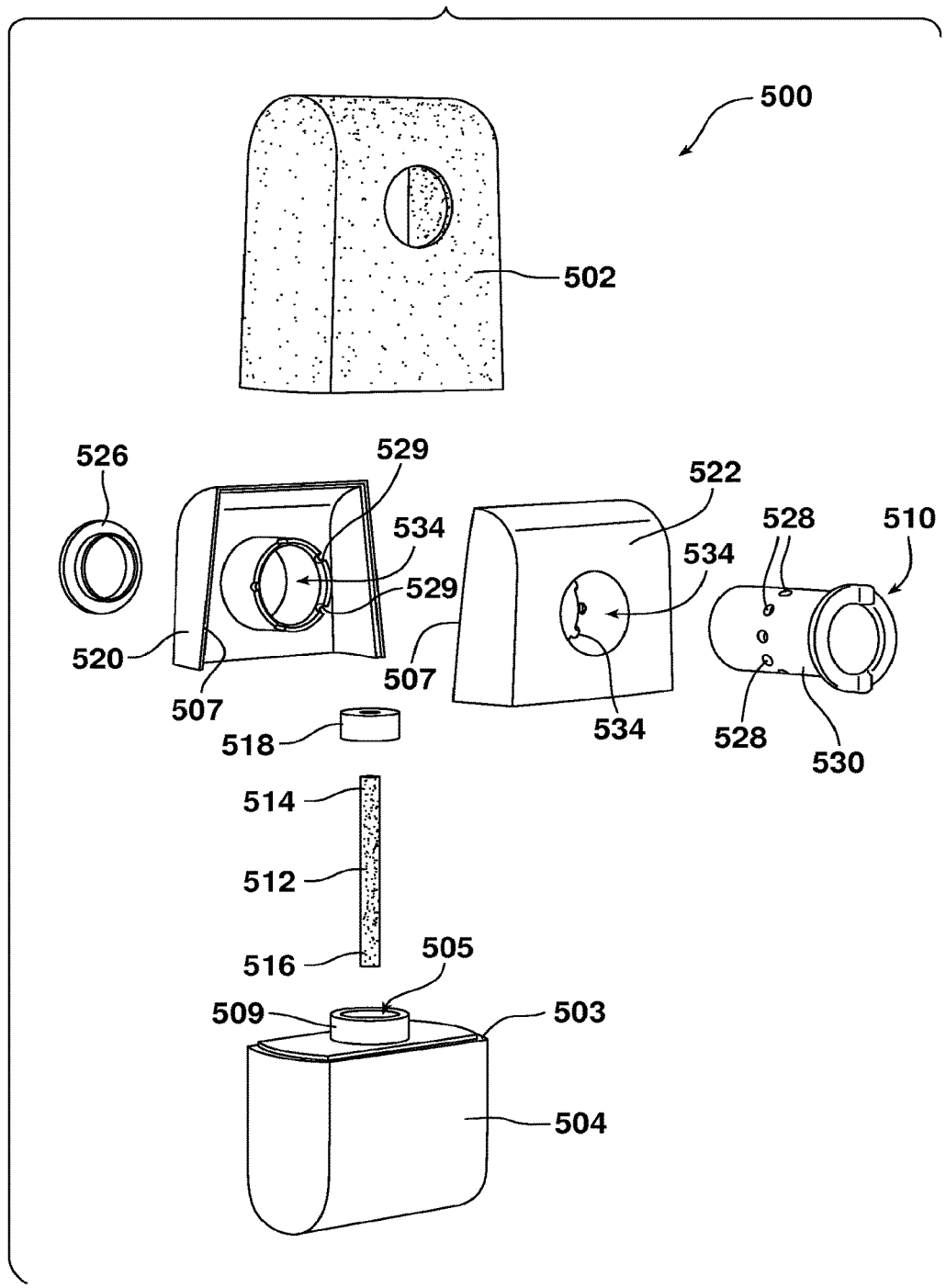

FIG. 19 is an exploded view showing all of the elements of the air freshener canister 500 depicted in this embodiment.

Figure 20:
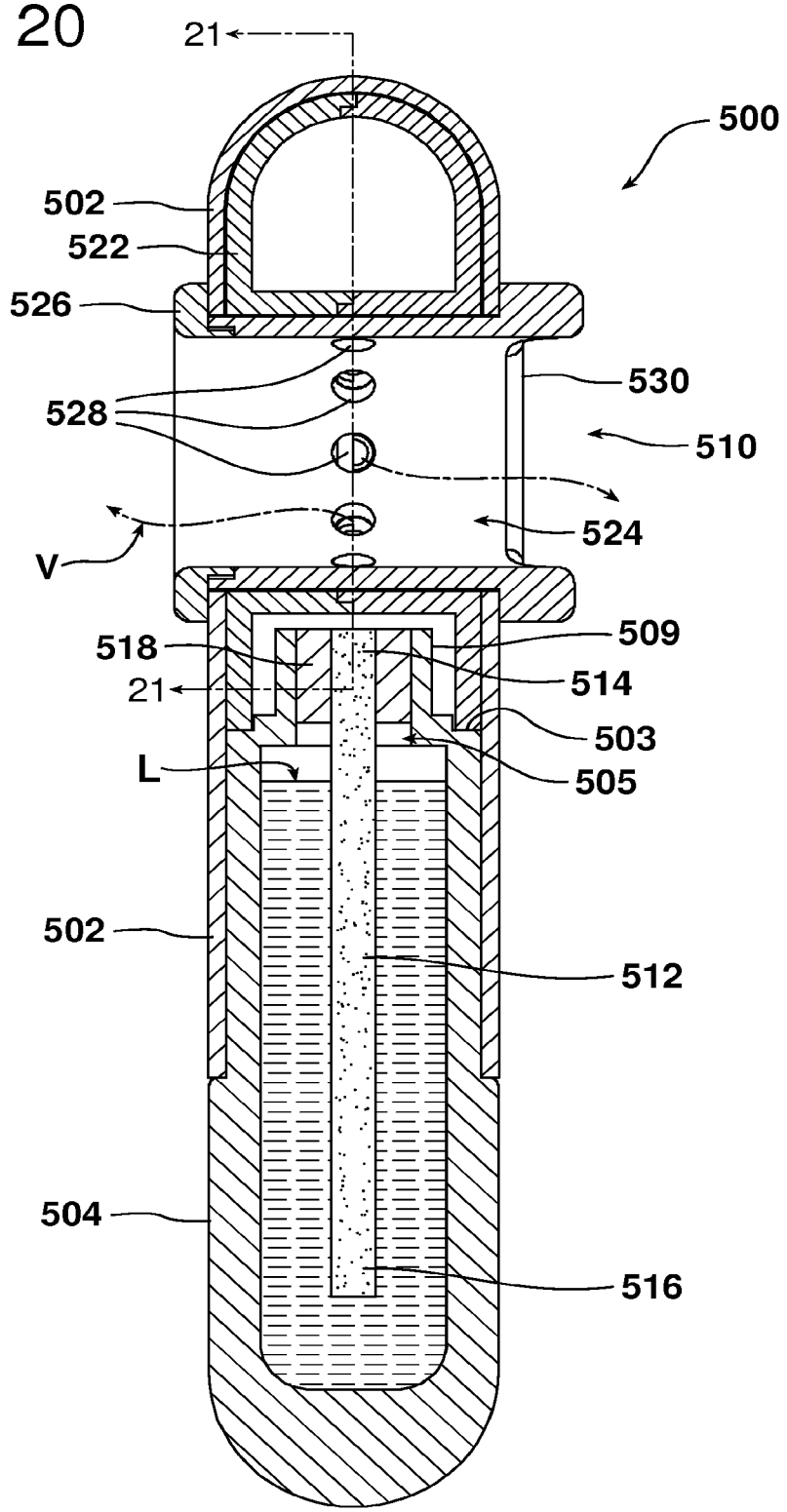

FIG. 20 is cross-sectional view taken along lines 20-20 of FIG. 17 with the air freshener canister 500 in the open position to permit the escape of vapor V from the canister.

Figure 21:
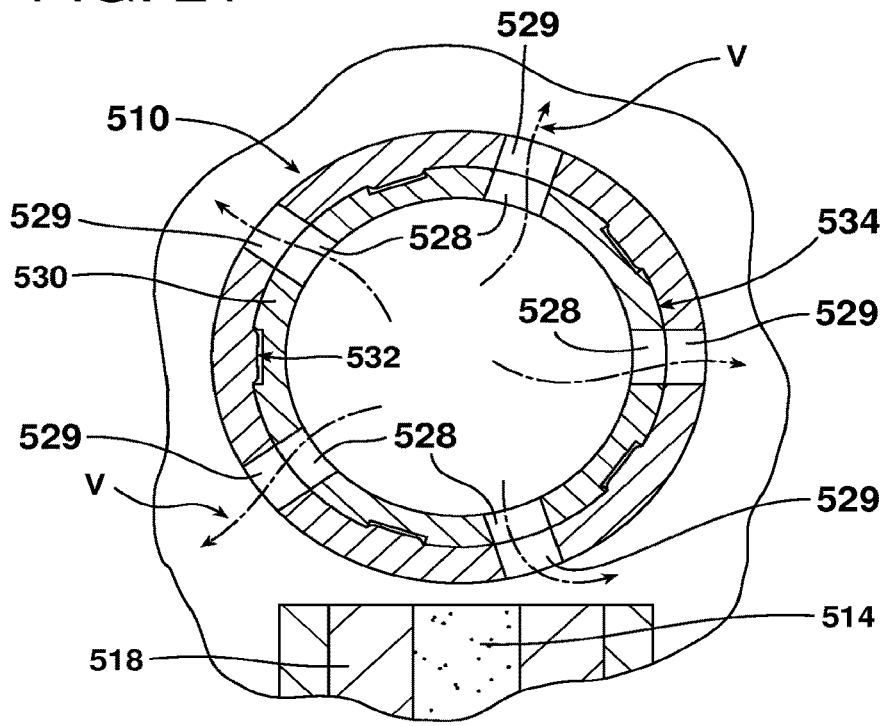

FIG. 21 is cross-sectional view taken along lines 21-21 of FIG. 20 with the air freshener canister 500 in the open position to permit the escape of vapor V from the canister.

Figure 22:
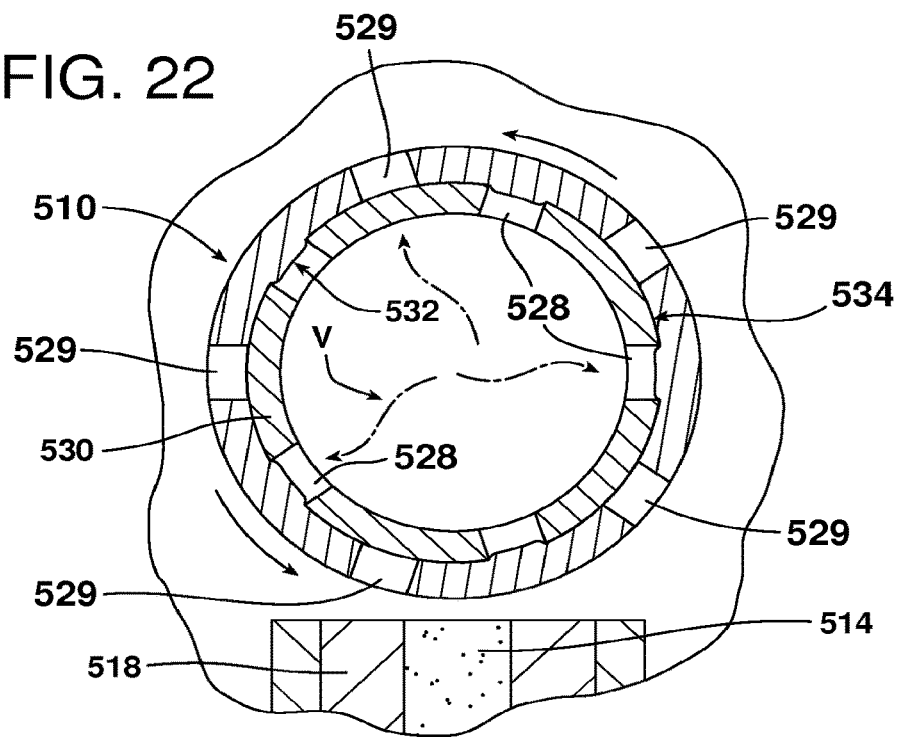

FIG. 22 is cross-sectional view taken along lines 21-21 of FIG. 20 with the air freshener canister in the closed position to permit the escape of vapor V from the canister.

The drawings are not presented to scale but are only used to illustrate the principles of the invention. In the drawings, like reference numbers indicate like elements.

DESCRIPTION OF THE INVENTION

A detailed description of one or more embodiments is provided below along with accompanying figures that illustrate the principles of the embodiments. The scope of the embodiments is limited only by the claims and encompasses numerous alternatives, modifications and equivalents. Numerous specific details are set forth in the following description. These details are provided solely for the purposes of example and the embodiments may be practiced according to the claims without some or all of these specific details.

First Embodiment: Medallion Air Freshener Canister

A first embodiment for this invention, the Medallion Air Freshener Canister, is shown in FIGS. 1 through 6.

Figure 1:
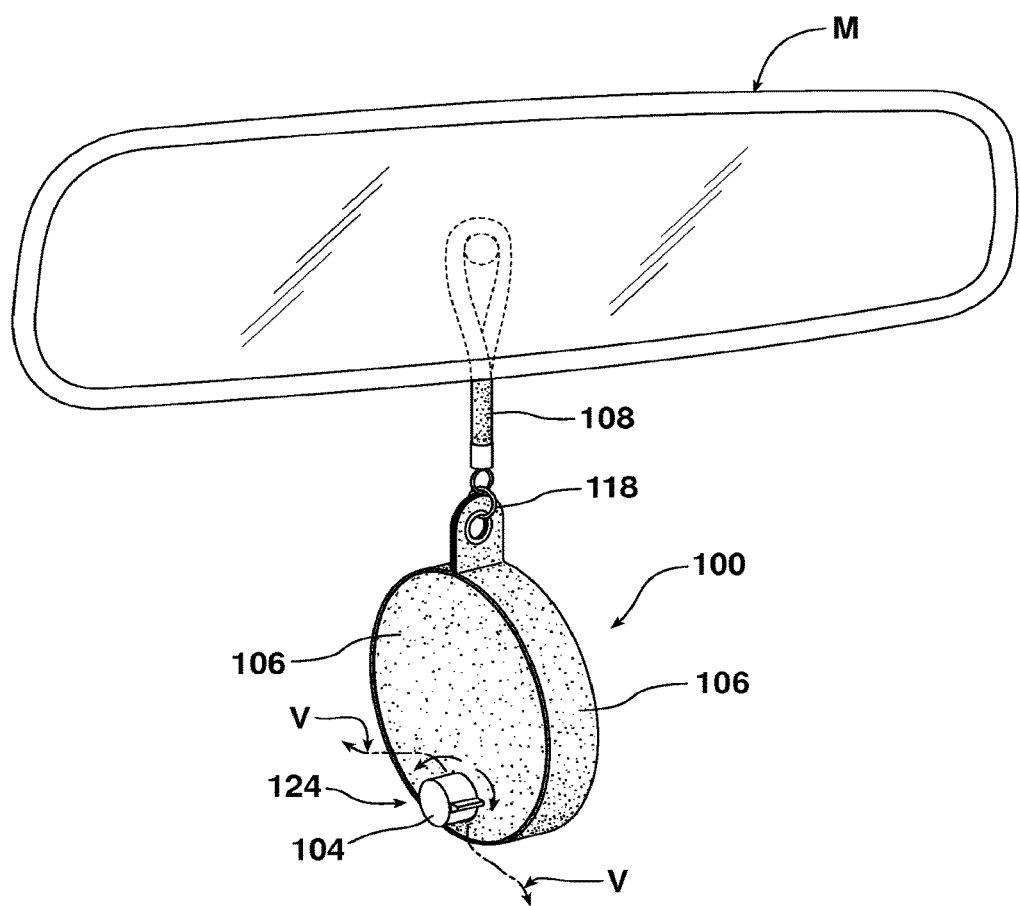
FIG. 1 is front perspective view of the Medallion Air Freshener Canister 100 in use suspended by a cord 108 from the rear view mirror M of an automobile.
Figure 4:
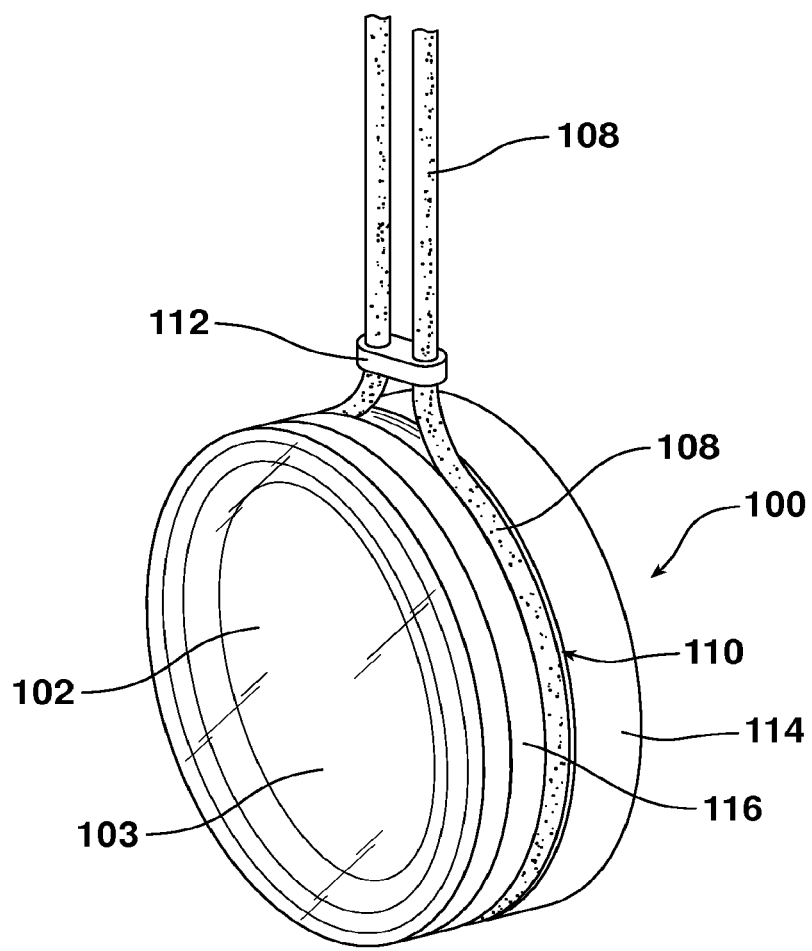
FIG. 4 is rear perspective view of the air freshener canister 100 depicted in FIGS. 1 and 2 with another type cord 108 for suspension of the canister 100 at a location, e.g., rear view mirror.

Referring for example to FIG. 1, this embodiment the air freshener canister 100 includes a means for suspending the air freshener from an object. In the embodiment shown a cord 108 suspends the canister 100 from the rear view mirror M of an automobile. FIG. 4 is a perspective view of the front of the air freshener canister 100 of this invention using a different type cord 108 for suspending from an object, e.g., automobile rear view mirror M. Optionally, the air freshener canister may be placed or mounted on a flat surface.

Figure 6A:
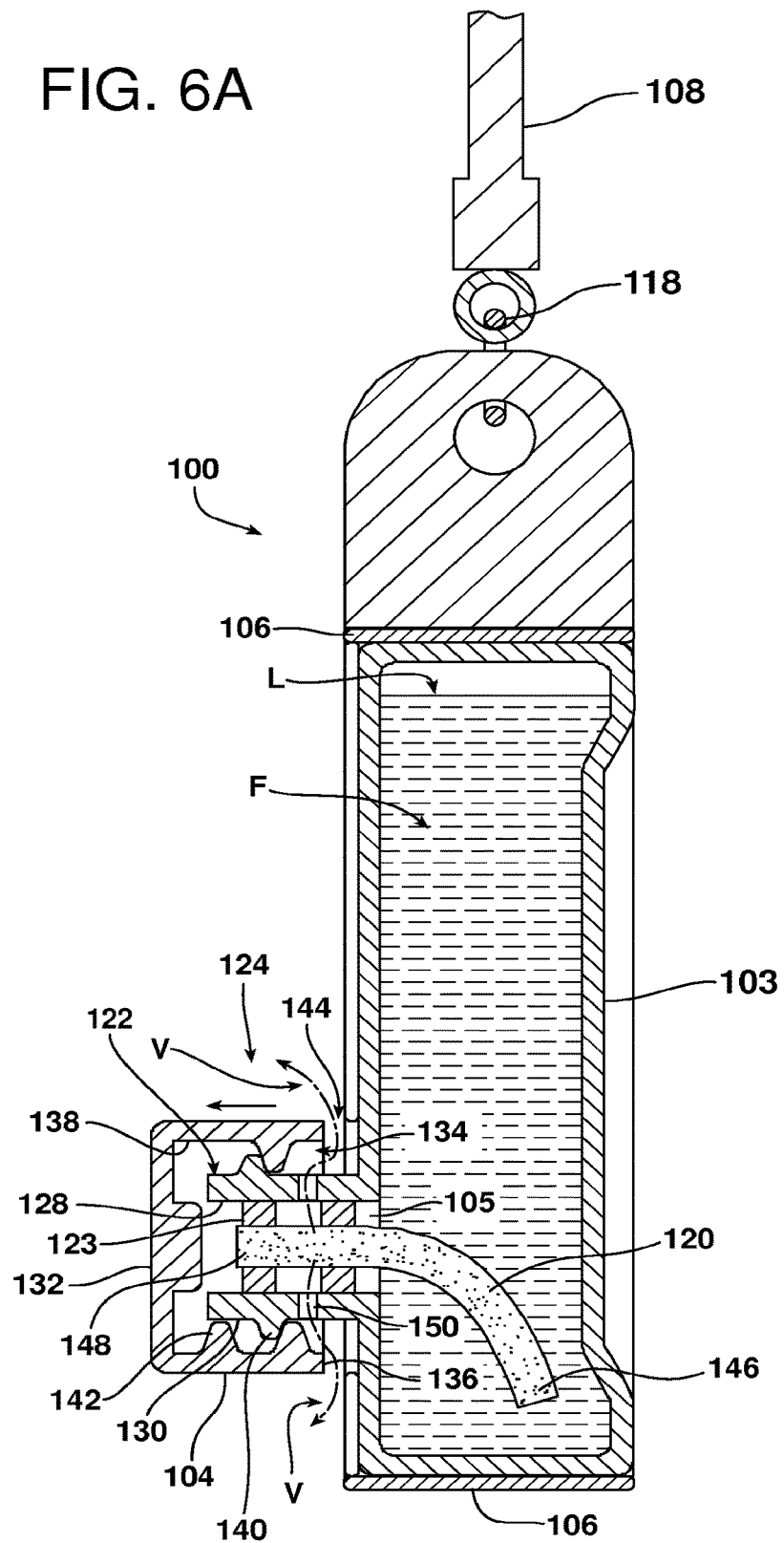
FIG. 6A is cross-sectional taken along lines 6-6 of FIG. 2 with the air freshener canister 100 in the open position to permit the escape of vapor V from the canister.
Figure 6B:
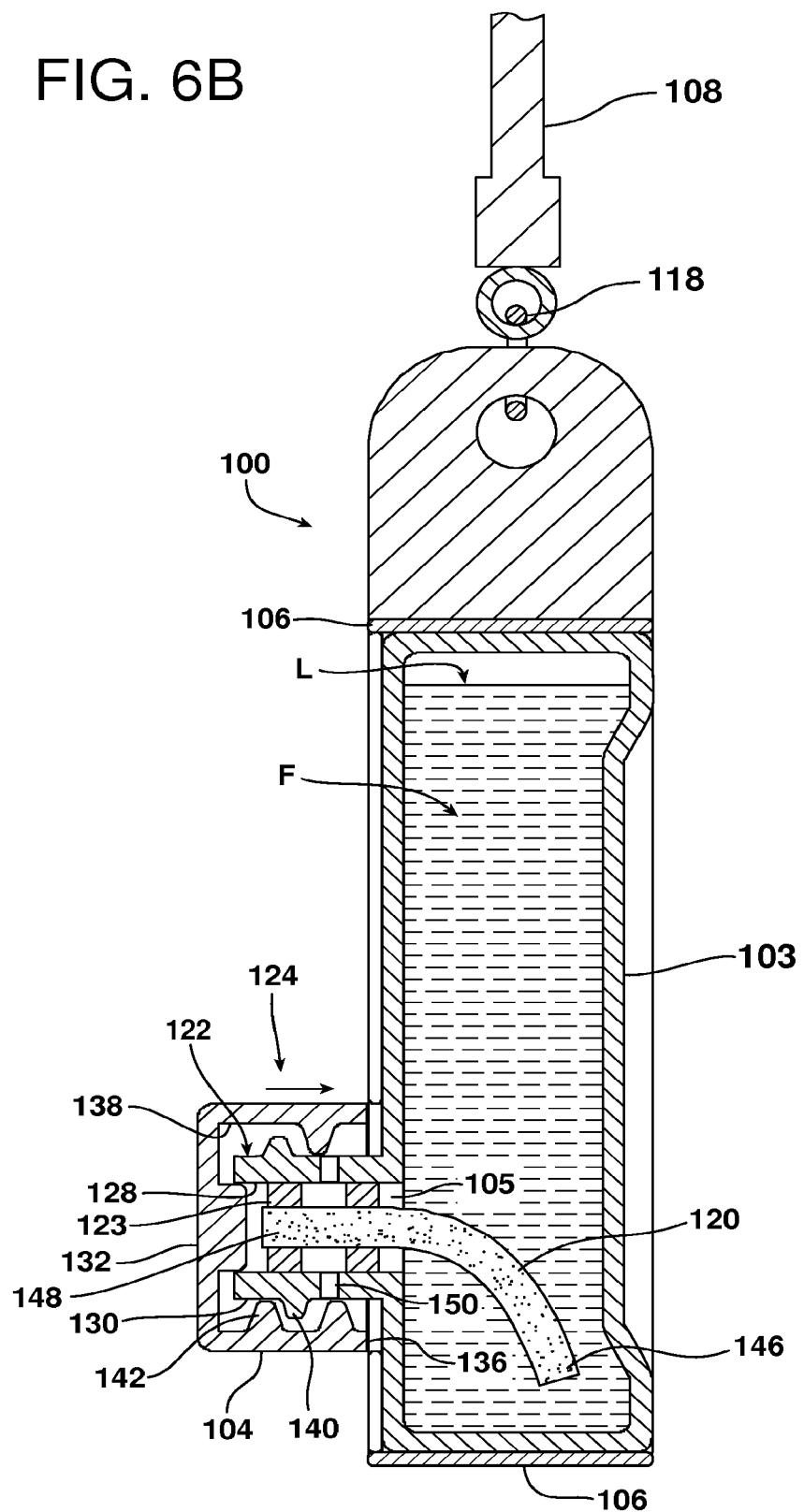
FIG. 6B is cross-sectional taken along lines 6-6 of FIG. 2 with the air freshener canister 100 in the closed position to prevent the escape of vapor V from the canister.

Referring, for example, to FIGS. 5, 6A and 6B, the air freshener canister 100 is provided with a container 102 into which a volatile liquid composition L may be placed. The volatile liquid composition L is capable of emitting air freshener vapor V at ambient conditions. The container 102 has an exterior surface 103 and a mouth opening 105 through the exterior surface 103. The container 102 in this embodiment, as well as all the other embodiments described herein, may be made of glass, plastic materials of adequate durability and tolerance, such as polypropylene or polyethylene terephthalate, or any other material suitable for containing the volatile liquid composition L and functioning with the other elements of this invention.

Referring to FIGS. 6A and 6B, a nipple 122 is on the exterior surface 103 of the container 102 and extends from the mouth opening 105. The nipple 122 can be attached, e.g., glued, welded, screwed on to the surface 103 to surround the mouth opening 105 or molded with the container 102 to form a one piece molded structure.

The nipple 122 has an interior surface 128 and an exterior surface 130. A cap or knob 104 is provided that has a closed end 132, an open end 134, a rim 136 around the open end 134 and an interior surface 138. In its simplest form the cap 104 is an on-off control. In a more sophisticated version as depicted herein it can moderate the strength of the air freshener vapors V emanating from the canister 100.

The interior surface 138 of the cap 104 is slidably engagable with the exterior surface 130 of the nipple 126. Preferably, as shown in FIGS. 6A and 6B, the exterior surface 130 of the nipple 126 has a first set of threads 140. A second set of threads 142 are provided on the interior surface 138 of the cap 104. These threads 140, 142 are slidably engagable with each other to enable the cap 104 to be selectively positioned along the nipple 122 by, in the embodiment shown, turning the cap (or knob) 104 clockwise or counter-clockwise, e.g., see FIGS. 1 and 2, arrows. Optionally, the cap 104 can frictionally engage the nipple 122 or another configuration of threads can be used.

Referring to 6B, the cap 104 may be selectively positioned between a closed position wherein the rim 136 is juxtaposed against the exterior surface 103 of the container 102. This may be accomplished by turning knob (cap) 104 clockwise to tighten the cap 104 on the nipple 126.

Referring to 6A, alternatively, the cap 104 may be turned counter-clockwise to an open position wherein there is a spacing 144 between the rim 136 of the cap 104 and the exterior surface 103 of the container 102.

Optionally, when necessary the cap 104 may be completely removed from the nipple 126 to enable the container 102 to be refilled with the volatile liquid L through the nipple 126.

Referring to FIGS. 6A and 6B, a wick 120 is provided for absorbing the volatile liquid composition L. The wick 120 has a length, a first end 146 and second end 148. The first end 146 and a first portion of the length of the wick 120 is surrounded by and in contact with the volatile liquid composition L, and the second end 148 and the remaining portion of the wick extend into the nipple 126. Optionally, as shown in FIGS. 5, 6A and 6B a wick holder 122 may be provided on the interior of the nipple 126 to maintain the second end 148 of the wick within the nipple 126. The wick holder 122 may be removed when the canister 100 is being refilled with liquid L and, if needed, a new wick 120 may be inserted.

Referring to FIG. 6A, when the cap 104 is in the open position air freshener vapors V escape from the volatile liquid composition L absorbed on the wick 120 through the spacing 144 between the rim 136 and the exterior surface 103 of the container 102 into the air. Referring to 6B, when the cap 104 is in the closed position air freshener vapors V are prevented from escaping. When the cap 104 is removed the container 102 may be refilled with the volatile liquid composition L.

As can be seen, the spacing 144 between the rim 136 and exterior surface 103 of the container 102 may be increased or decreased by selectively positioning the cap 104 on the nipple 126 to thereby increase or decrease the escape of air freshener vapors through the spacing 144 into the air.

In the preferred embodiment depicted in FIGS. 6A and 6B a vent hole 150 is provided in the nipple 122 that extends from the interior surface 128 to the exterior surface 130 of the nipple 126 and permits the passage of air freshener vapors V therethrough. Several vent holes 150 may be provided around the circumference and length of the nipple 122. The numbering and positioning of the vent holes 150 along the length and circumference control to a large extent the selective control over the quantity of vapors emitted into the air. The more air vents 150 that are exposed to the atmosphere, by exposing them on the nipple 122, the higher the rate of evaporation into the atmosphere.

Optionally, as shown on in the Figures for this embodiment, the container 102 glass and is surrounded by a cover 106 preferably decorative, having a cord 108 connected to it to permit the hanging of the canister 100 from parts of the car, e.g., rear view mirror M, coat hook, etc.

Referring to FIG. 4, the air freshener canister 100 has a groove 110 around the cylindrical canister 100 into which the cord 108 for hanging fits. As depicted, a clasp 112 surrounds the cord 108 and enables it to be tightened to secure the canister 100 or loosened to remove the canister 100 from the cord 108 for, for example, for refilling the canister 100.

The air freshener canister 100 in this embodiment (and all the others described herein) may have a cover 106 whose surface texture and color may be easily changed by replacing it with another cover 106. The decorative cover 106 may be selected, for example, to match the upholstery of the car or blend with the upholstery in a decorative manner. The decorative cover 106 can be a branded cover, such as a Gucci® or Coach® branded fabric or leather, or can have thereon the brand or decorative fabric of the brand of the automobile, e.g., Volkswagen, BMW, Jaguar, etc. There are numerous possibilities. When a transparent container 102 is used and left uncovered, the amount of volatile liquid composition L remaining in the container may be seen.

The volatile composition L used in this embodiment, as well as the others embodiments described herein, can be any of the well-known air freshener liquids or optionally a branded perfume, Chanel #5®, Old Spice®, etc. Optionally, the decorative cover 106 can match the brand of air freshener used in the canister 100. The compositions may have different scents, such as pine, cinnamon, pineapple, lavender, and other scents as well as odor neutralizers and aromatherapy compositions. The compositions may include oils such as artificial air fresheners, essential oils, aromatherapy oils or the like. The composition may also be in the form of a liquid or a gel, e.g., a slow release gel, or a variable release gel, a volatile gel or is a slow release gel, a controlled release gel or the like or a similar form of a composition. Scented inserts may also be used in the container. The inserts can be comprised of a variety of materials, such as scented gel material, cotton, fabric, or sponge, e.g., an open-cell sponge material which is configured to substantially occupy the internal cavity of the container.

In this embodiment and all other embodiments described herein, the compositions may also be in the form of refills, inserts, replaceable cartridges, cassettes, packages or the like in which the individual containers can be replenished easily with a custom made replacement that fit easily in the container when it is time to renew the air freshener so that the container can be reused without having to purchase new containers.

Second Embodiment: Tear Drop Air Freshener Canister

A second embodiment for this invention, the Tear Drop Air Freshener Canister is shown in FIGS. 7 through 9.

Referring for example to FIG. 7, in this embodiment the air freshener canister 200 includes a means for suspending the air freshener from an object. In the embodiment shown a cord 208 suspends the canister 200 from the rear view mirror M of an automobile.

Referring to FIGS. 7-9, the air freshener canister 200 is provided with a tear drop shaped container 204 into which a volatile liquid composition L may be placed, see FIG. 9A, 9B. The volatile liquid composition is capable of emitting air freshener vapor V at ambient conditions. The container has a mouth opening 205. The container 204 may be made of glass, or plastic materials of adequate durability and tolerance, such as polypropylene or polyethylene terephthalate or any other material suitable for containing the volatile liquid composition L and functioning with the other elements of this invention. A preferred material for this embodiment is wood, primarily for its decorative features.

Referring to FIGS. 8, 9A and 9B, a cap 206 is mounted to the mouth opening 205. The cap 206 may screw on or snap on the mouth 205 for easy removal to refill the canister 200.

The cap 206 has an interior surface 228, a nipple 209 extending therefrom and an exterior surface 230 thereon. A knob 202 is provided that has an open end 234, a rim 236 around the open end 234 and an interior surface 238. In its simplest form the knob 202 is an on-off control. In a more sophisticated version as depicted herein it can moderate the strength of the air freshener vapors V emanating from the canister 200.

The interior surface 238 of the knob 202 is slidably engagable with the exterior surface 230 of the nipple 209 of cap 206. Preferably, as shown in FIGS. 9A and 9B, the exterior surface 230 of the nipple 209 has a first set of threads 240. A second set of threads 242 are provided on the interior surface 238 of the knob 202. These threads 240, 242 are slidably engagable with each other to enable the knob 202 to be selectively positioned along the nipple 209, in the embodiment shown, by turning the knob 202 clockwise or counter-clockwise. Optionally, the knob 202 can frictionally engage the nipple 209 or another configuration of threads can be used.

The knob 202 may be selectively positioned to a closed position, see FIG. 9A wherein the rim 236 of the knob 202 is juxtaposed against the shoulder surface 207 of the top of cap 206. This may be accomplished by turning knob 202 clockwise on the nipple 209 to tighten the knob 202 on the exterior surface 230 of nipple 209.

Alternatively, as shown in FIG. 9B the knob 202 may be turned counter-clockwise to an open position wherein there is a spacing 220 between the rim 236 of the knob 202 and the shoulder surface 207 of the cap 206.

Optionally, when necessary the knob 202 may be completely removed with the cap 206 to enable the container 204 to be refilled with the volatile liquid L through the mouth opening 205.

Referring to FIGS. 8, 9A and 9B, a wick 214 is provided for absorbing the volatile liquid composition L. The wick 214 has a length, a first end 218 and second end 216. The first end 218 and a first portion of the length of the wick 214 is surrounded by and in contact with the volatile liquid composition L, and the second end 216 and the remaining portion of the wick extend into the cap 206 and nipple 209. Optionally, a wick holder (not shown in this embodiment) may be provided on the interior of the cap 206 to maintain the second end 216 of the wick 214 within the cap 206.

Referring to FIG. 9B, when the knob 202 is in the open position air freshener vapors V escape from the volatile liquid composition L absorbed on the wick 214 through the spacing 220 between the rim 236 and the shoulder surface 207 of the cap 206 into the air. Referring to 9A, when the knob 202 is in the closed position air freshener vapors V are prevented from escaping. When the cap 207 is removed the container 204 may be refilled with the volatile liquid composition L and/or the wick 214 replaced.

Referring to FIGS. 9A and 9B, as can be seen, the spacing 220 between the rim 236 and shoulder surface 207 of the cap 206 may be increased or decreased by selectively positioning the knob 202 on the nipple 209 to thereby increase or decrease the escape of air freshener vapors through the spacing 220 into the air.

In the preferred embodiment, referring to FIGS. 8, 9A and 9B a vent hole 250 is provided in the nipple 209 that extends from the interior surface 228 of the nipple 209 to the exterior surface 230 of the nipple 209 and permits the passage of air freshener vapors V therethrough. Several vent holes 250 may be provided around the circumference and length of the nipple 209. The numbering and positioning of the vent holes 250 along the length and circumference control to a large extent the selective control over the quantity of vapors emitted into the air.

Optionally, the container 202 is surrounded by a cover, preferably decorative (not shown in this embodiment). Additionally, a cord 208 passes through the knob 202 and is connected to the top of the nipple 209. Such a structure permits the knob 209 to be turned while the canister 200 is hanging, e.g., from the rear view mirror M, coat hook, etc.

Third Embodiment: Dashboard-Front Window Canister

A third embodiment for this invention, the Front Dash Board Air Freshener Canister is shown in FIGS. 10 through 13.

Referring for example to FIGS. 10 and 11, this embodiment the air freshener canister 300 is shaped and designed to be place on the front dashboard D of the car, and optionally wedged between the window W and dashboard D.

Referring to FIGS. 10-13, the air freshener canister 300 is provided with a pyramid shaped, truncated or wedge shaped canister 300 consisting of a container 302 into which a volatile liquid composition L is placed, see FIGS. 13A and 13B. The volatile liquid composition is capable of emitting air freshener vapor V at ambient conditions. The container has a mouth opening 305. The container 302 may be made of glass, or plastic materials of adequate durability and tolerance, such as polypropylene or polyethylene terephthalate or any other material suitable for containing the volatile liquid composition L and functioning with the other elements of this invention.

Referring to FIGS. 12, 13A and 13B, the canister 300 further includes a cap 304 having a top surface 307 and a bottom surface 310. The cap 304 is mounted to the mouth opening 305. The cap 304 may screw on or snap on the mouth 305 for easy removal to refill the canister 300.

In the preferred embodiment, the container 302 has a top surface 312 a nipple 309 extending therefrom surrounding the mouth opening 305. The cap 304 has an open end 334 through the bottom surface 310 and an interior surface 338. In its simplest form the cap 304 is an on-off control. In a more sophisticated version as depicted herein it can moderate the strength of the air freshener vapors V emanating from the canister 300.

The interior surface 338 of the cap 304 is slidably engagable with the exterior surface 330 of the nipple 309 of container 302. Preferably, as shown in FIGS. 13A and 13B, the exterior surface 330 of the nipple 309 has a first set of threads 340. A second set of threads 342 are provided on the interior surface 338 of the open end 334 of the cap 304. These threads 340, 342 are slidably engagable with each other to enable the cap 302 to be selectively positioned along the nipple 309 by, in the embodiment shown, by turning the cap 302 clockwise or counter-clockwise. Optionally, the cap 302 can frictionally engage the nipple 309 or another configuration of threads can be used.

The cap 302 may be selectively positioned to a closed position, see FIG. 13A wherein the bottom surface 310 of the cap 302 is juxtaposed against the top surface 312 of the container 302. This may be accomplished by turning the cap 302 clockwise on the nipple 309 to tighten the cap 302 on the exterior surface 330 of nipple 309.

Alternatively, as shown in FIG. 13B the cap 302 may be turned counter-clockwise to an open position wherein there is a spacing 308 between the top surface 312 of container 302 and the bottom surface 310 of the cap 304.

Optionally, when necessary the cap 302 may be completely removed to enable the container 302 to be refilled with the volatile liquid L through the mouth opening 305.

Referring to FIGS. 12, 13A and 13B, a wick 306 is provided for absorbing the volatile liquid composition L. The wick 306 has a length, a first end 318 and second end 316. The first end 318 and a first portion of the length of the wick 306 is surrounded by and in contact with the volatile liquid composition L, and the second end 316 and the remaining portion of the wick extend into the cap 304 and nipple 309. Optionally, a wick holder (not shown in this embodiment) may be provided on the interior of the nipple 309 to maintain the second end 316 of the wick 306 within the cap 304.

Referring to FIG. 13B, when the cap 302 is in the open position air freshener vapors V escape from the volatile liquid composition L absorbed on the wick 306 through the spacing 308 between the surfaces 310 and 312. Referring to 13A, when the cap 304 is in the closed position air freshener vapors V are prevented from escaping. When the cap 304 is removed the container 302 may be refilled with the volatile liquid composition L and/or the wick 306 replaced.

Referring to FIGS. 13A and 13B, as can be seen, the spacing 308 between the surfaces 310 and 312 may be increased or decreased by selectively positioning the cap 304 on the nipple 309 to thereby increase or decrease the escape of air freshener vapors through the spacing 308 into the air.

In the preferred embodiment, referring to FIGS. 13A and 13B a vent hole 350 is provided in the nipple 209 that extends from the interior surface 228 of the nipple 309 to the exterior surface 330 of the nipple 309 and permits the passage of air freshener vapors V therethrough. Several vent holes 350 may be provided around the circumference and length of the nipple 309. The numbering and positioning of the vent holes 350 along the length and circumference control to a large extent the selective control over the quantity of vapors emitted into the air.

The cap 304 may be made of or coated with a resilient, gripping polymer or rubber to enable the canister 300 to grip the window W and/or dashboard D to maintain the canister 300 in place.

Fourth Embodiment: Dashboard Air Freshener Canister

A fourth embodiment for this invention, the Dash Board Air Freshener Canister is shown in FIGS. 14 through 16.

Referring for example to FIGS. 14 and 15, this embodiment of the air freshener canister 400 is disc shaped and designed to be placed on a flat surface, e.g., the front dashboard D of the car near the front window W or on a table or wall.

The air freshener canister 400 shown is disc shaped, but can be any shape that provides the functionality of this embodiment. The canister 400 consists of a container 402 and a base 404. The container 402 may be made of glass, or plastic materials of adequate durability and tolerance, such as polypropylene or polyethylene terephthalate or any other material suitable for containing a volatile composition F and functioning with the other elements of this invention.

Referring to FIGS. 16A and 16B, the container 402 preferably contains a solid volatile air freshener composition F that can be, for example, a gel, such as a slow release gel, or a variable release gel. The volatile solid composition F is capable of emitting air freshener vapor V at ambient conditions. The composition F may also be in the form of refills, inserts, replaceable cartridges, cassettes, packages or the like for insertion into the container 402 that can be replenished easily when it is time to renew the air freshener so that the container can be reused without having to purchase new containers. The insert can be constructed of a variety of materials, such as scented gel material, cotton, fabric, or sponge, e.g., an open-cell sponge material which is configured to substantially occupy the internal cavity of the container 402. The container 402 may also be disposable or interchangeable with different fragrances.

Referring to FIGS. 16A and 16B, the canister 400 includes the container 402 having a top surface 407 and a bottom surface 409. The container 402 has at least one, and a preferably a plurality of vents 403 in the bottom surface 409 that extends through the bottom surface 409 of the container 402 and permits the passage of air freshener vapors V therethrough. The number and positioning of the vent holes 403 in the bottom surface 409 of the container 402 control, to a large extent the selective control over the quantity of vapors V emitted into the air. In the preferred embodiment, the container 402 has a nipple 411 extending from the bottom surface 409.

The base 404 of the canister 400 has a top surface 414 and a bottom surface 416. The top surface 414 of the base 404 has hole 417 therein which may, but not necessarily, extend through to the bottom surface 416.

The nipple 411 on the container 402 has an exterior surface 438 that is slidably engagable with the interior surface 430 of the hole 417 in the base 404. Preferably, as shown in FIGS. 16A and 16B, the exterior surface 438 of the nipple 411 has a first set of threads 440. A second set of threads 442 are provided on the interior surface 430 of the hole 417 in the top surface 414 of the base 404. These threads 440, 442 are slidably engagable with each other to enable the base 404 to be selectively positioned along the nipple 411, in the embodiment shown, by turning the container 402 clockwise or counter-clockwise. Optionally, the base 404 can frictionally engage the nipple 411, or another configuration of threads can be used. In its simplest form the coaction of the container 402 with the base 404 is an on-off control. In a more sophisticated version, as depicted herein, this coaction can moderate the strength of the air freshener vapors V emanating from the canister 400.

Referring to FIGS. 16A and 16B, the base 404 and container 402 may be selectively positioned to a closed position wherein the bottom surface 409 of the container 402 is juxtaposed against the top surface 312 of the base 404. This may be accomplished by turning the container 402 clockwise to tighten the container 402 to draw the surfaces 409 and 414 together (FIG. 16A).

Alternatively, the container 402 may be turned counter-clockwise to an open position wherein there is a spacing 412 between the top surface 414 of the base 404 and the bottom surface 409 of the container 404 (FIG. 16B).

Optionally, when necessary the container 402 may be completely removed to enable the container 402 to be refilled or replaced with the volatile solid F.

Referring to FIG. 16B, when the container 402 is in the open position air freshener vapors V escape from the volatile solid composition F through the vents 403 and then through the spacing 412 between the surfaces 409 and 414. Referring to 16A, when the container 404 is in the closed position air freshener vapors V are prevented from escaping.

Referring to FIGS. 16A and 16B, as can be seen, the spacing 412 between the surfaces 409 and 414 may be increased or decreased by selectively positioning the container 404 on the nipple 411 to thereby increase or decrease the escape of air freshener vapors through the spacing 412 into the air.

The base 404 may be made of or coated with a resilient, gripping polymer or rubber to enable the canister 400 to grip the dashboard D to maintain the canister 400 in place. Preferably, as indicated in FIGS. 15, 16A and 16B, there is a mounting means consisting of at least one suction cup 406, and preferably two suction cops 406 attached to the bottom surface 416 of the base 404 to hold the canister 400 in place on a flat surface, e.g., dashboard, wall, table.

Fifth Embodiment: Convertible Air Freshener Canister

A fifth embodiment for this invention, the Convertible Air Freshener Canister, is shown in FIGS. 17 through 22.

Referring for example to FIG. 17, this embodiment of the air freshener canister 500 includes a means for suspending the air freshener 500 from an object. In the embodiment shown a cord 506 passes through opening 524 and suspends the canister 500 from the rear view mirror M of an automobile. Generally, 510 is the control mechanism and/or the on-off mechanism to control the volatile vapors V in this embodiment.

Referring to FIG. 18, the canister 500 may have, in addition to or as an alternative, an attachment means, such as a suction cup 508 mounted to a face of the canister 500 for attachment to a flat surface, such as the dashboard D of an automobile.

Referring to FIGS. 17-22, the air freshener canister 500 is provided with a container 504 into which a volatile liquid composition L may be placed, see FIG. 20. The volatile liquid composition is capable of emitting air freshener vapor V at ambient conditions. The container has a mouth opening 505. The container 504 may be made of glass, or plastic materials of adequate durability and tolerance, such as polypropylene or polyethylene terephthalate or any other material suitable for containing the volatile liquid composition L and functioning with the other elements of this invention.

Referring to FIGS. 19 and 20, a two piece cap 520 and 522 is mounted to the lip 503, surrounding a nipple the mouth opening 505. The cap pieces 520 and 522 making up the cap, may be permanently or removable attached to each other along cap lips 507 and are designed to be removable as a unit from the lip 503 on the container 504 for easy refill the canister 500 container 504.

Referring to FIGS. 19 and 20, a wick 512 is provided for absorbing the volatile liquid composition L. The wick 512 has a length, a first end 516 and a second end 514. The first end 516 and a first portion of the length of the wick 512 is surrounded by and in contact with the volatile liquid composition L, and the second end 514 and the remaining portion of the wick extends into the mouth 505 of the container 503 and the nipple 509 atop the mouth. Optionally, a wick holder 518 may be provided on the interior of the nipple 509 and/or mouth 505 to maintain the second end 514 of the wick 512 within the mouth 505 and nipple 509.

Referring to FIG. 20, the cap structure 520, 522 is removably engagable with the exterior surface of the container 504. The structure encloses the mouth 505 and the nipple 509. The cap structure 520, 522 further includes a cylindrical passageway 534 therethrough having at least one vent hole 529, and preferably a plurality of such vent holes 529, that permit the passage of air freshener vapors V therethrough from the wick 512.

Referring to FIGS. 20-22, the canister 500 further includes a drum 530 rotatably engagable within the cylindrical passageway 534. The drum, 530 has at least one vent hole 528, and preferably a plurality of such vent holes 528. The drum 530 is selectively rotatable from an open position, see FIGS. 20 and 21 and a closed position, see FIG. 22. In the open position, FIG. 21, the vent holes 529 in the cap and the vent holes 528 in the drum 530 are aligned to permit the passage of air freshener vapors V therethrough into the air. When the drum 530 is rotated to the closed position the holes, 528, 529 are not aligned preventing the passage of air vapors therethrough. The number and location of the vent holes, 528 and 529, may be arranged to permit selective alignment of the vent holes 528, 529 to provide a graduated increase or decrease of the escape of air freshener vapors V into the air.

Optionally, as shown in FIG. 21 and FIG. 22 the drum 530 and passage way 534 can have at least one detent structure 532 that snaps into position, for example when the canister 500 is off, on and/or at different levels.

Optionally, the cap structure 520, 522 is surrounded by a cover, preferably decorative 502.

The invention has been described with reference to various specific and illustrative aspects of the present invention and techniques. However, it should be understood that many variations and modifications may be made while remaining within the spirit and scope of the invention. Many alternatives, modifications and variations will be apparent to those skilled in the art in light of the foregoing description. Accordingly, this invention is intended to embrace all such alternatives, modifications, and variations that fall within the spirit and scope of the appended claims.

What is claimed is:

1. An air freshener canister comprising:
   a container for containing an air freshener substance, the container having an opening;

a cap removably mounted to the opening of the container, the cap having a shoulder;

a nipple extending from the shoulder of the cap, the nipple comprising an interior surface, an exterior surface, and at least one vent extending from the interior surface to the exterior surface; and a knob, the knob comprising a rim, the knob being engageable with the exterior surface of the nipple in at least a first position and a second position;

wherein in the first position the rim of the knob abuts the shoulder of the cap; and wherein in the second position there is a spacing between the rim of the knob and the shoulder of the cap such that air freshener vapors can escape from the air freshener canister through the at least one vent.

2. The air freshener canister of claim 1, wherein the cap is screwably mounted to the opening of the container.

3. The air freshener canister of claim 1, wherein the cap is snappably mounted to the opening of the container.

4. The air freshener canister of claim 1, wherein the air freshener substance comprises a volatile liquid that is refillable through the opening of the container.

5. The air freshener canister of claim 1, wherein the knob further comprises an interior surface, and wherein screw threads on the interior surface of the knob are engageable with screw threads on the exterior surface of the nipple.

6. The air freshener canister of claim 1, wherein the knob is removable from the nipple.

7. The air freshener canister of claim 1, wherein the spacing between the rim of the knob and the shoulder of the cap is adjustable to increase or decrease a rate of escape of the air freshener vapors from the air freshener canister through the at least one vent.

8. The air freshener canister of claim 1, wherein the nipple comprises a plurality of vents disposed around a circumference and a length of the nipple.

9. The air freshener canister of claim 8, wherein the spacing between the rim of the knob and the shoulder of the cap is adjustable to increase or decrease a rate of escape of the air freshener vapors from the air freshener canister through the plurality of vents.

10. The air freshener canister of claim 1, wherein the knob comprises a bottom opening defined by the rim, and a top opening, and wherein at least a portion of the nipple extends through the top opening of the knob.

11. The air freshener canister of claim 10, wherein a cord passes through a portion of the nipple extending through the top opening of the knob for hanging the air freshener canister.

12. The air freshener canister of claim 1, wherein the air freshener substance comprises a volatile liquid, and wherein the air freshener canister further comprises a wick, the wick having a length, a first end and a second end, wherein the first end and a first portion of the length of the wick are surrounded by and in contact with the volatile liquid, and wherein the second end and a second portion of the wick are disposed in the cap.

13. The air freshener canister of claim 12, further comprising a wick holder for holding the second end of the wick within the cap.

\* \* \* \* \*